United States Patent
Kalinski

(10) Patent No.: US 7,655,216 B2
(45) Date of Patent: Feb. 2, 2010

(54) VACCINE FOR ACTIVATING HELPER FUNCTION OF CD8+ TCELLS

(75) Inventor: Pawel Kalinski, Wexford, PA (US)

(73) Assignee: University of Pittsburgh - Of the Commonwealth of Higher Education, Pittsburgh, PA (US)

( * ) Notice: Subject to any disclaimer, the term of this patent is extended or adjusted under 35 U.S.C. 154(b) by 0 days.

(21) Appl. No.: 12/037,294

(22) Filed: Feb. 26, 2008

(65) Prior Publication Data

US 2008/0206280 A1 Aug. 28, 2008

Related U.S. Application Data

(60) Provisional application No. 60/891,670, filed on Feb. 26, 2007.

(51) Int. Cl.
  A61K 49/00 (2006.01)
  A61K 39/38 (2006.01)
  A61K 38/00 (2006.01)
  C07K 14/00 (2006.01)

(52) U.S. Cl. ............... 424/9.1; 424/9.2; 424/184.1; 530/300; 530/350

(58) Field of Classification Search ............... 424/9.1, 424/9.2, 184.1; 530/300, 350
See application file for complete search history.

(56) References Cited

U.S. PATENT DOCUMENTS

| | | | |
|---|---|---|---|
| 4,832,959 | A | 5/1989 | Engels et al. |
| 5,437,994 | A | 8/1995 | Emerson et al. |
| 5,605,822 | A | 2/1997 | Emerson et al. |
| 5,624,895 | A | 4/1997 | Sobel |
| 5,635,386 | A | 6/1997 | Palsson et al. |
| 5,646,043 | A | 7/1997 | Emerson et al. |
| 5,670,147 | A | 9/1997 | Emerson et al. |
| 5,670,351 | A | 9/1997 | Emerson et al. |
| 5,763,215 | A | 6/1998 | Blumberg et al. |
| 5,763,266 | A | 6/1998 | Palsson et al. |
| 5,780,021 | A | 7/1998 | Sobel |
| 6,204,022 | B1 | 3/2001 | Johnson et al. |
| 6,326,198 | B1 | 12/2001 | Emerson et al. |
| 2005/0003533 | A1 | 1/2005 | Kalinski |
| 2006/0051354 | A1 | 3/2006 | Simard et al. |

FOREIGN PATENT DOCUMENTS

| | | |
|---|---|---|
| WO | WO 02/053176 A2 | 7/2002 |
| WO | WO 02/088328 A2 | 11/2002 |
| WO | WO 2005/011729 A1 | 2/2005 |

OTHER PUBLICATIONS

Watchmaker, P.B., et al. Journal of Immunology, vol. 180, No. 6, pp. 3857-3865, Mar. 2008.*
Nakamura, Y., et al. Cancer Research, vol. 67, No. 20, pp. 10012-10018, Oct. 2007.*
Albert et al., Nature Immunology, 2(11): 1010-1017 (Nov. 2001).
Alexopoulou et al., Nature, 413(6857): 732-738 (Oct. 18, 2001).
Asselin-Paturel et al., The Journal of Experimental Medicine, 202(4): 461-465 (Aug. 15, 2005).
Badovinac et al., Immunity, 18: 463-474 (Apr. 2003).
Badovinac et al., Nature Medicine, 11(7): 748-756 (Jul. 2005).
Bajt et al., Toxicological Sciences, 58(1): 109-117 (Nov. 2000).
Bajt et al., Toxicology and Applied Pharmacology, 175(3): 243-252 (Sep. 15, 2001).
Banchereau et al., Nature, 392(6673): 245-252 (Mar 19, 1998).
Belz et al., Proc. Natl. Acad. Sci. USA, 104(15): 6341-6346 (Apr. 10, 2007).
Bennett et al., Nature, 393: 478-480 (Jun. 4, 1998).
Berke et al., Immunology, 78: 105-112 (1993).
Berke, Immunology Reviews, 146: 21-31 (Aug. 1995).
Betz et al., The Journal of Immunology, 146(1): 108-113 (Jan. 1, 1991).
Bhardwaj, The Journal of Experimental Medicine, 186(6): 795-799 (Sep. 15, 1997).
Bladergroen et al., The Journal of Immunology, 166:3218-3225 (2001).
Casado et al., Cancer Immunology Immunotherapy 54(12): 1162-1171 (Dec. 2005).
Cella et al., The Journal of Experimental Medicine, 184(2): 747-752 (Aug. 1996).
Chikamatsu et al., Clinical Cancer Research, 5(6): 1281-1288 (Jun. 1999).
Colonna et al., Nature Immunology, 5(12): 1219-1229 (Dec. 2004).
David, Pharmacology & Therapeutics, 65(2): 149-161 (1995).
De Jong et al., The Journal of Immunology, 168(4): 1704-1709 (Feb. 15, 2002).
Del Prete et al., The Journal of Experimental Medicine, 174(4): 809-813 (Oct. 1, 1991).
De Smedt et al., European Journal of Immunology, 27(5): 1229-1235 (Mar. 1997).
Dhodapkar et al., The Journal of Experimental Medicine, 193(2): 233-238 (Jan. 15, 2001).
Eardley et al., The Journal of Experimental Medicine, 142: 524-529 (1975).
Endharti et al., The Journal of Immunology, 175: 7093-7097 (2005).
Feng et al., European Journal of Pharmacology, 481: 169-173 (2003).

(Continued)

Primary Examiner—Rodney P. Swartz
(74) Attorney, Agent, or Firm—Klarquist Sparkman, LLP

(57) ABSTRACT

The invention provides compositions and methods for treating or preventing a target disease in a mammal by induction of memory T cells. The methods comprise (1) administering a sensitizing composition comprising a non-target antigen to a patient; and (2) administering a therapeutic composition comprising a non-target antigen and a target antigen to the patient, wherein the target antigen is associated with the disease, and wherein the therapeutic composition is administered after the sensitizing compositions, at an interval sufficient for induction of memory T cells. The methods can alternatively comprise administering a target antigen along with an inhibitory agent such as an inhibitor of DC apoptosis, an inhibitor of Granzyme B, a Granzyme-B-inducible mediator of apoptosis, an inhibitor of perforin, or a perforin-inducible mediator of apoptosis.

21 Claims, 11 Drawing Sheets

OTHER PUBLICATIONS

Figure 1:
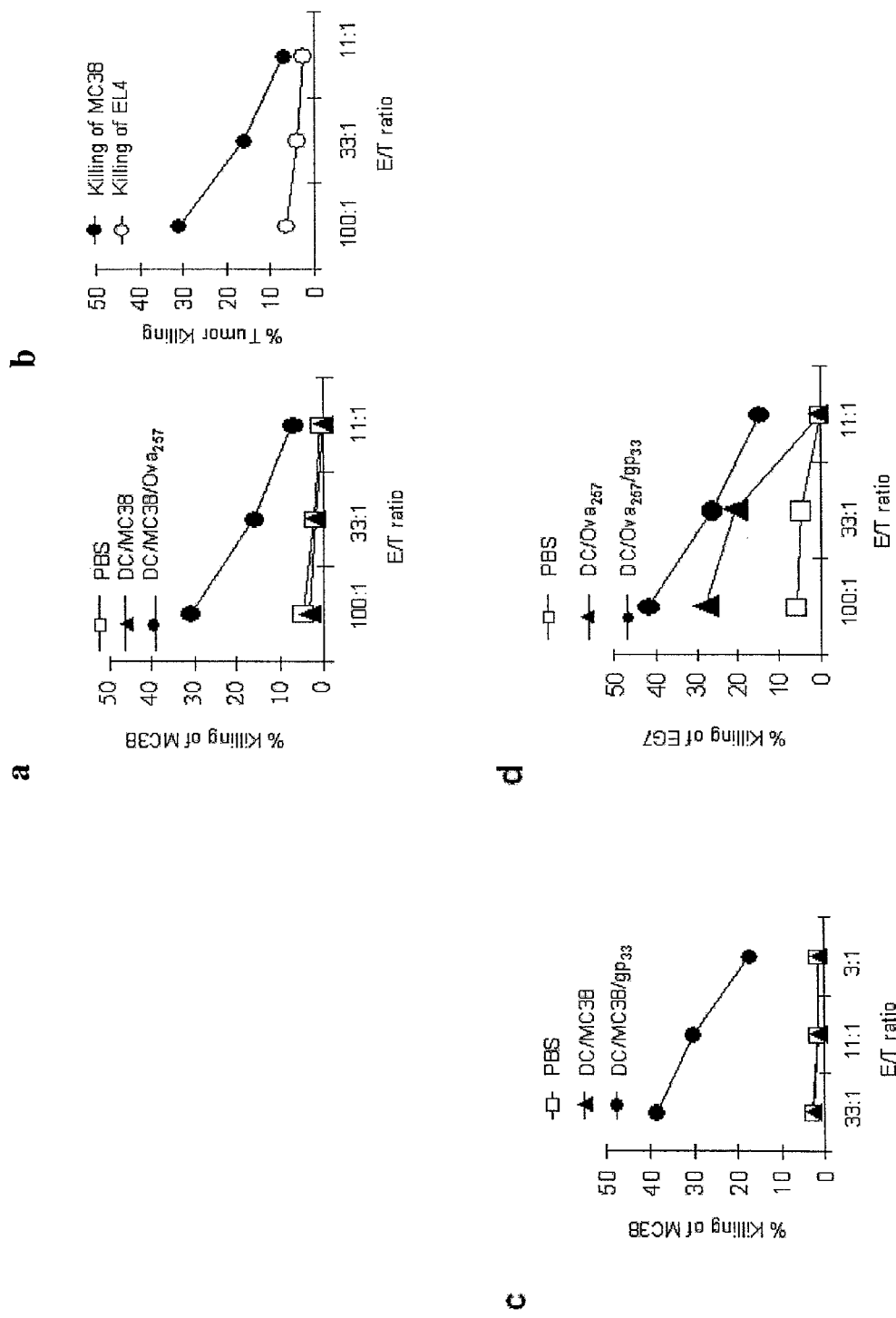

Fraser, *Research in Immunology*, 144(3): 173-174 (1993).
Friberg et al., *Method*, 9(2): 316-326 (Apr. 1996).
Gallucci et al., *Nature Medicine*, 5(11): 1249-1255 (Nov. 1999).
Gattinoni et al., *The Journal of Clinical Investigation*, 115(6): 1616-1626 (Jun. 2005).
Gattinoni et al., *Nature Reviews, Immunology*, 6: 383-393 (May 2006).
Gershon et al., *The Journal of Immunology*, 108(3): 586-590 (Mar. 1972).
Gilliet et al., *The Journal of Experimental Medicine*, 195(6): 695-704 (Mar. 18, 2002).
Grossman et al., *Immunity*, 21(4): 589-601 (Oct. 2004).
Guarda et al., *Nature Immunology*, 8(7): 743-752 (Jul. 2007).
Gurunathan et al., *The Journal of Experimental Medicine*, 186(7): 1137-1147 (Oct. 6, 1997).
Gurunathan et al., *The Journal of Immunology*, 165: 915-924 (2000).
Hafalla et al., *The Journal of Immunology*, 171: 964-970 (2003).
Harris et al., *Trends in Immunology*, 29(3): 144-150 (Mar. 2002).
Hayashida et al., *Proceedings of the Society for Experimental Biology and Medicine*, 225(2): 143-150 (Nov. 2000).
Hermans et al., *The Journal of Immunology*, 164: 3095-3101 (2000).
Hernandez et al., *The Journal of Immunology*, 178: 2844-2852 (2007).
Hilkens et al., *Blood*, 90(5): 1920-1926 (Sep. 1, 1997).
Hirschhorn et al., *Science*, 142: 1185-1187 (Nov. 29, 1963).
Janssen et al., *Nature*, 421: 852-856 (Feb. 20, 2003).
Jonuleit et al., *European Journal of Immunology*, 27(12): 3135-3142 (Dec. 1997).
Jonuleit et al., *The Journal of Experimental Medicine*, 192(9): 1213-1222 (Nov. 6, 2000).
Jonuleit et al., *International Journal of Cancer*, 93(2): 243-251 (2001).
Ju et al., *Proceedings of the National Academy of Sciences of the United States of America*, 91(10): 4185-4189 (May 10, 1994).
Kaech et al., *Nature Reviews*, 2: 251-262 (Apr. 2002).
Kagi et al., *Science*, 265: 528-530 (Jul. 22, 1994).
Kalinski et al., *The Journal of Immunology*, 154(8): 3753-3760 (Apr. 15, 1995).
Kalinski et al., *The Journal of Immunology*, 159(1): 28-35 (Jul. 1, 1997).
Kalinski et al., *The Journal of Immunology*, 161(6): 2804-2809 (Sep. 15, 1998).
Kalinski et al., *The Journal of Immunology*, 162(6): 3231-3236 (Mar. 15, 1999).
Kalinski et al, *Immunolgy Today*, 20(12): 561-567 (Dec. 1999).
Kalinski et al., *The Journal of Immunology*, 165(4): 1877-1881 (Aug. 15, 2000).
Kalinski et al., *Blood*, 97(11): 3466-3469 (Jun. 1, 2001).
Kalinski, National Institute of Health Grant Application No. 1 RO01 CA095128 entitled "Polarization of Dendritic Cells by CD8+ T Cells" (2007).
Kanto et al., *The Journal of Immunology*, 167: 3773-3784 (2001).
Karaghiosoff et al., *Nature Immunology*, 4(5): 471-477(May 2003).
Kataoka et al., *The Journal of Immunology*, 165: 3678-3686 (1996).
Kim et al., *Cancer Research*, 64: 400-405 (Jan. 1, 2004).
Klebanoff et al., *PNAS*, 102(27): 9571-9576 (Jul. 5, 2005).
Kogawa et al., *Blood*, 99(1): 61-66 (Jan. 1, 2002).
Krug et al., *European Journal of Immunology*, 31(10): 3026-3037 (Oct. 2001).
Langenkamp et al., *Nature Immunology*, 1(4): 311-316 (Oct. 2000)
Lanzavecchia et al., *Science*, 290(5489): 92-97 (Oct. 6, 2000).
Lanzavecchia et al., *Nature*, 2: 982-987 (Dec. 2002).
Lu et al., *The Journal of Immunology*, 172(7): 4575-4582 (Apr. 1, 2004).
Ludewig et al., *European Journal of Immunology*, 31: 1772-1779 (2001).
Luft et al., *Blood*, 100(4): 1362-1372 (Aug. 15, 2002).
Maczek et al., *International Journal of Cancer*, 115: 450-455 (2005).
Mailliard et al., *Journal of Experimental Medicine*, 195(4): 473-483 (Feb. 18, 2002).
Mailliard et al., *Cancer Research*, 64(17): 5934-5937 (Sep. 1, 2004).
Marzo et al., *Nature Immunology*, 6(8): 793-790 (Aug. 2005).
Mattner et al., *European Journal of Immunology*, 26(7): 1553-1559 (Jul. 1996).
McKenna et al., *Journal of Virology*, 79(1): 17-27 (Jan. 2005).
McRae et al., *The Journal of Immunology*, 160(9): 4298-4304 (May 1, 1998).
Medema et al., *Journal of Experimental Medicine*, 194(5): 657-667 (Sep. 3, 2001).
Meng et al., *The Journal of Immunology*, 177(3): 1981-1987 (Aug. 1, 2006).
Messi et al., *Nature Immunology*, 4(1): 78-86 (Jan. 2003).
Mintern et al., *The Journal of Immunology*, 168: 977-980 (2002).
Mueller et al., *The Journal of Immunology*, 176:7379-7384 (2006).
Nakamura et al., *Cancer Research*, 67(20): 10012-10018 (Oct. 15, 2007).
NCBI, "Interferon, gamma," Database Entre Gene Accession No. 3458, (Jul. 20, 2008), Retrieved on Jul. 25, 2008.
NCBI, "Interferon, gamma [*Homo sapiens*]," Database Entre-Protein, Accession No. NP_000610 (Jul 20, 2008). Retrieved Jul. 25, 2008.
NCBI, "*Homo sapiens* interferon, gamma (IFNG), mRNA," Database Entre-Nucleotide, Accession No. NM_000619 (Jul. 20, 2008). Retrieved Jul. 25, 2008.
Nestle et al., *Nature Medicine*, 4(3): 328-332 (Mar. 1998).
OMIM, "Interferon, Gamma; IFNG," Database Online Medelian Inheritance in Man, Accession No. 147570 (Jul. 26, 2006). Retrieved Jul. 25, 2008.
OMIM "Interferon, Alpha-1; IFNA1," Database Online Medelian Inheritance in Man, Accession No. 147660 (Mar. 3, 2006). Retrieved Jul. 25, 2008.
Parmiani et al., *Journal of the National Cancer Institute*, 94(11): 805-818 (Jun. 5, 2002).
Peters et al., *Dendritic Cells in Fundamental and Clinical Immunology*, (Kamperdijk et al., eds.), 275-280 (Plenum Press, New York, NY, 1993).
Platanias et al., *Experimental Hematology*, 27(11): 1583-1592 (Nov. 1999).
Plate, *Nature*, 260(5549): 329-331 (Mar. 25, 1976).
Ramshaw et al., *Immunology Today*, 21(4): 163-165 (Apr. 2000).
Ridge et al., *Nature*, 393: 474-478 (Jun. 4, 1998).
Rissoan et al., *Science*, 283(5405): 1183-1186 (Feb. 19, 1999).
Rivino et al., *Journal of Experimental Medicine*, 200(6): 725-735 (Sep. 20, 2004).
Robinson et al., *Journal of the National Cancer Institute*, 57(3) 699-602 (Sep. 1976).
Ronchese et al, *Journal of Experimental Medicine*, 194(5): F23-F26 (Sep. 3, 2001).
Rosenberg et al., *Nature Medicine*, 10(9): 909-915 (Sep. 2004).
Ruedl et al., *Journal of Experimental Medicine*, 189(12): 1875-1883 (Jun. 21, 1999).
Sad et al., *Critical Reviews in Immunology*, 23(1 & 2): 129-147 (2003).
Sallusto et al., *The Journal of Experimental Medicine*, 179(4): 1109-1118 (Apr. 1, 1994).
Sallusto et al., *Nature*, 401(6754): 708-712 (Oct. 14, 1999).
Sallusto et al., *Curr Top Microbiol Immunol*, 251: 167-171 (2000).
Sallusto et al., *Annual Review of Immunology*, 18: 593-620 (2000).
Sallusto et al., *The Journal of Clinical Investigation*, 108(6): 805-806 (Sep. 2001).
Sallusto et al., *Annual Review of Immunology*, 22: 745-763 (2004).
Scandella et al., *Blood*, 100(4): 1354-1361 (Aug. 15, 2002).
Schijns et al., *The Journal of Immunology*, 160(8): 3958-3964 (Apr. 15, 1998).
Schoenberger et al., *Nature*, 393: 480-483 (Jun. 4, 1998).
Schreckenberger et al., *Current Opinion in Oncology*, 16: 485-491 (2004).
Schuler-Thurner et al., *The Journal of Immunology*, 165(6): 3492-3496 (Sep. 15, 2000).
Schuler-Thurner et al., *The Journal of Experimental Medicine*, 195(10): 1279-1288 (May 20, 2002).
Semenzato et al., *Cancer*, 48(10): 2191-2197 (Nov. 15, 1981).
Shedlock et al., *Science*, 300: 337-339 (Apr. 11, 2003).
Shevach, *Immunity*, 25: 195-201 (Aug. 2006).

Shi et al., *Nature*, 425: 516-521 (Oct. 2003).
Shimizu et al., *Journal of Pediatric Surgery*, 36(8): 1285-1292 (Aug. 2001).
Shurin et al., *Chemical Immunology*, 68: 153-174 (1997).
Smits et al., *The Journal of Immunolgy*, 168(4): 1710-1716 (Feb. 15, 2002).
Snijders et al., *International Immunology*, 10(11): 1593-1598 (1998).
Snijdewint et al., *The Journal of Immunology*, 150(12): 5321-5329 (Jun. 15, 1993).
Spearman, *Current Pharmaceutical Design*, 12(9): 1147-1167 (2006).
Sprent et al., *Annu. Rev. Immunol.*, 20: 251-579 (2002).
Srivastava, *Current Opinion in Immunology*, 18: 201-205 (2006).
Steinman et al., *International Journal of Cancer*, 94(4): 459-473 (2001).
Sun et al., *The Journal of Biological Chemistry*, 272(24): 15434-15441 (Jun. 13, 1997).
Sun et al., *Science*, 300: 339-342 (Apr. 11, 2003).
Tahara et al., *Cancer Research*, 54(1): 182-189 (Jan. 1, 1994).
Tatsumi et al., *The Journal of Experimental Medicine*, 196(5): 619-628 (Sep. 2, 2002).
Thomas et al., *The Journal of Immunology*, 168: 216-223 (2002).
Thornberry et al., *The Journal of Biological Chemistry*, 272(29): 17907-17911 (Jul. 18, 1997).
Thurner et al., *The Journal of Experimental Medicine*, 190(11): 1669-1678 (Dec. 6, 1999).
Tough, *Trends in Immunology*, 24(8): 404-407 (Aug. 2003).
Trinchieri, *International Reviews of Immunology*, 16(3-4): 365-396 (1998).
Trinchieri, *Advances in Immunolgy*, 70: 83-243 (1998).
Trinchieri, *Nature Reviews*, 3: 133-146 (Feb. 2003).
Tschopp, *Annu. Rev. Immunol.*, 8: 279-302 (1990).
Tsukishiro et al., *Cancer Immunology Immunotherapy*, 52: 599-607 (2003).
Turner et al., *Journal of Virology*, 81(4): 2039-2046 (Feb. 2007).
Tüting et al., *The Journal of Immunology*, 160(3): 1139-1147.
Van Der Pouw Kraan et al., *The Journal of Experimental Medicine*, 181(2): 775-779 (Feb. 1, 1995).
Verdijk et al., *The Journal of Immunology*, 163(1): 57-61 (Jul. 1, 1999).
Vieira et al., *The Jouranl of Immunology*, 164(9): 4507-4512 (May 1, 2000).
Wang et al., *The Journal of Immunology*, 167: 1283-1289 (2001).
Watchmaker et al., *The Journal of Immunology*, 180(6): 3857-3865 (2008).
Williams et al., *Immunological Reviews*, 211: 146-153 (2006).
Wherry et al. *Nature Immunology*, 4(3): 225-234 Mar. 2003.
Wherry et al., *Journal of Virology*, 79(14): 8960-8968 (Jul. 2005).
Wierenga et al., *The Journal of Immunology*, 147(9): 2942-2949 (Nov. 1, 1991).
Wong et al., *Immunity*, 18: 499-511 (Apr. 2003).
Woodland, *Trends in Immunology*, 25(2): 98-104 (Feb. 2004).
Yang et al., *Proc. Natl. Acad. Sci. USA*, 103(1): 147-152 (Jan. 3, 2006).
Zhu et al., *Journal of Translational Medicine*, 5(10): 1-15 (Feb. 12, 2007).
Zitvogel et al., *The Journal of Experimental Medicine*, 183(1): 87-97 (Jan. 1, 1996).
Watchmaker et al., *Journal of Immunotherapy*, 29(6): 657 (Nov./Dec. 2006).

* cited by examiner

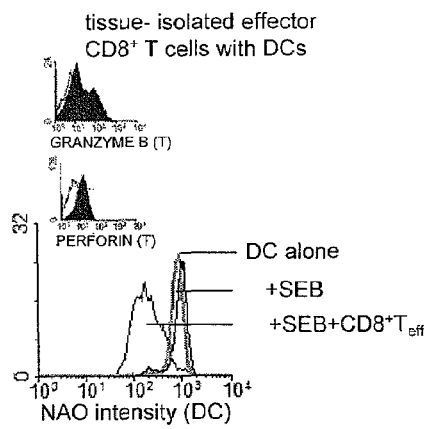
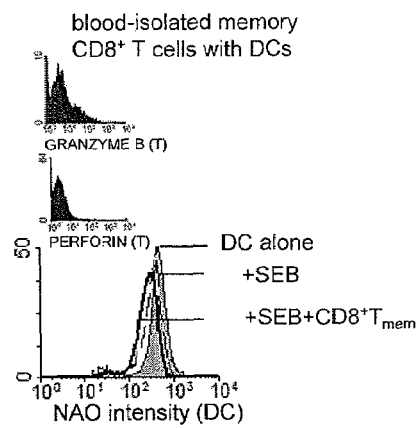
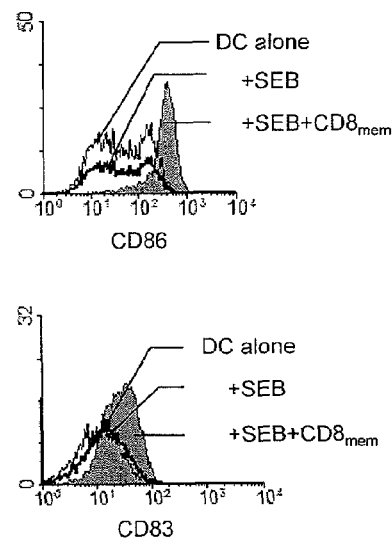
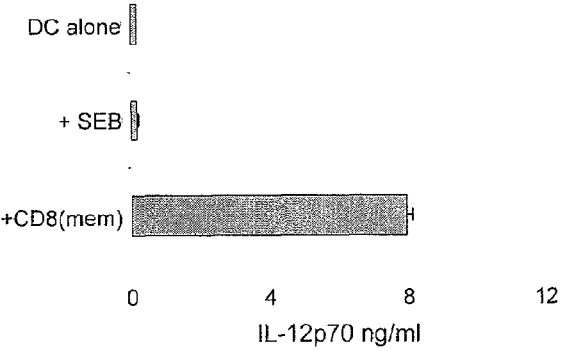
FIGURE 5

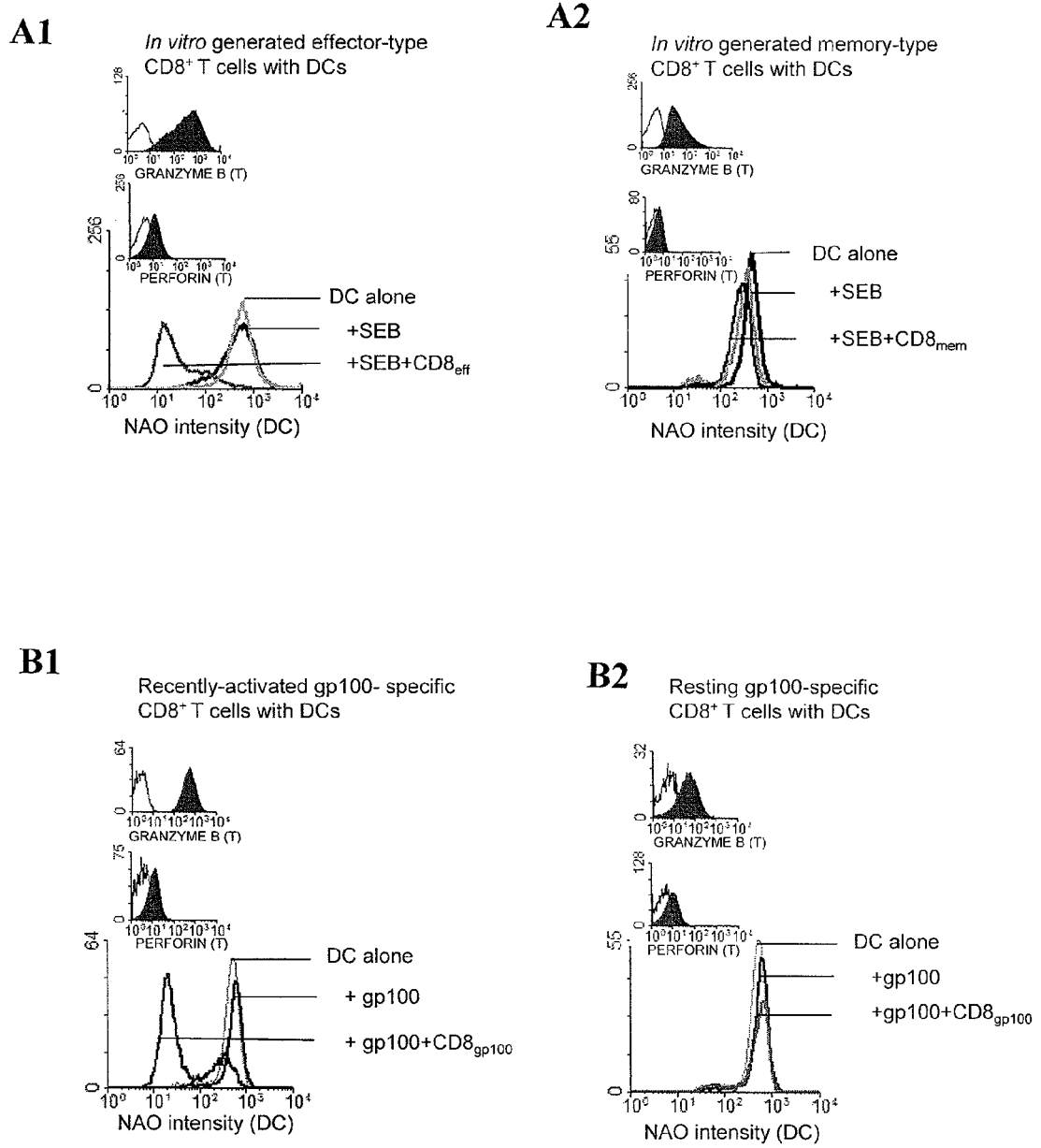
FIGURE 6-I

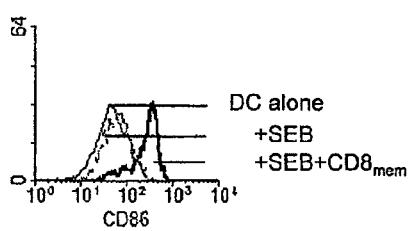
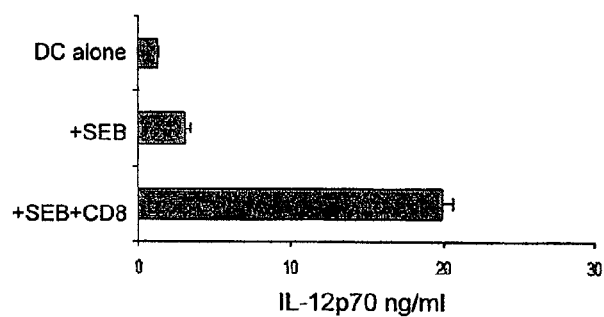
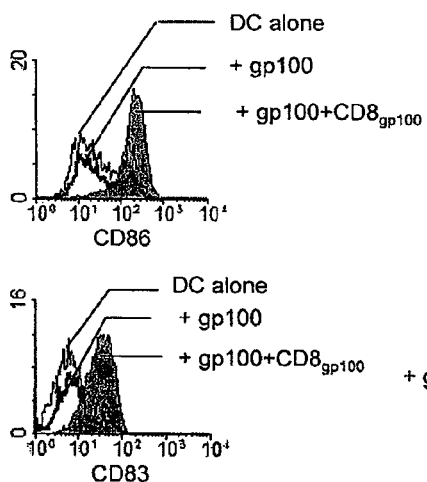
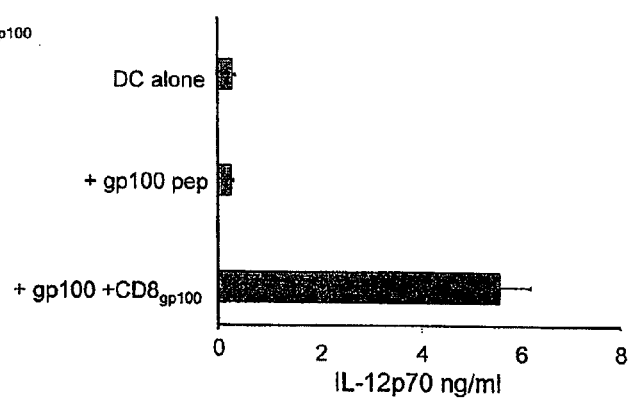
FIGURE 6-II

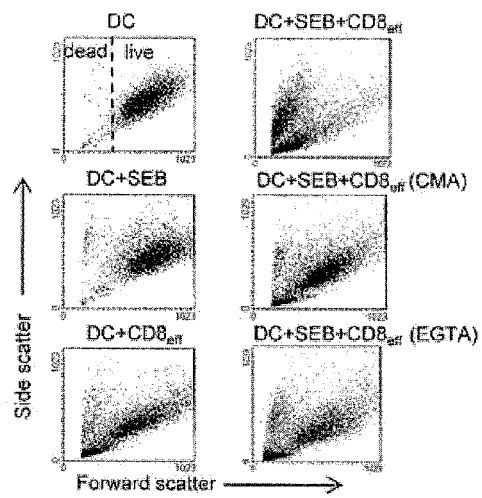
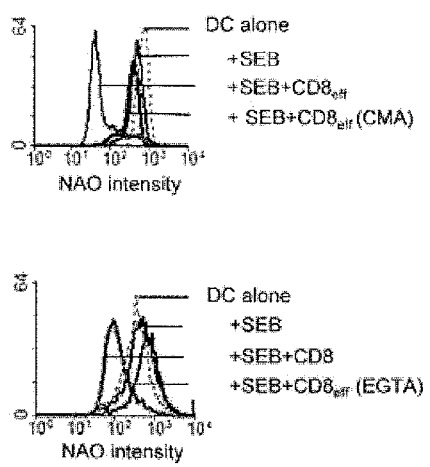
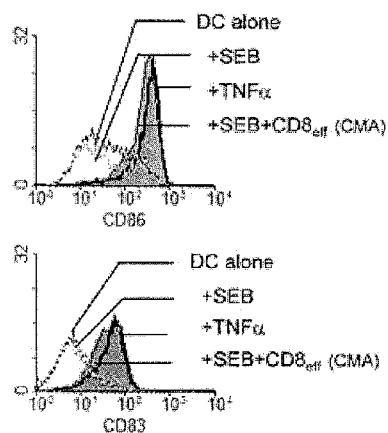
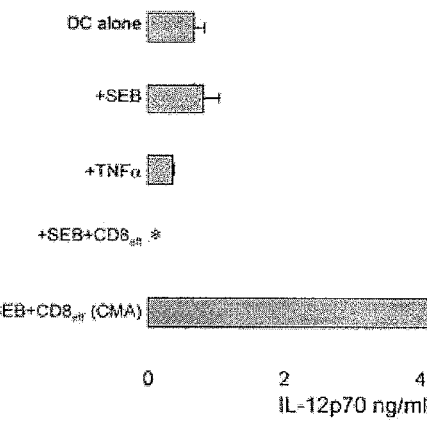
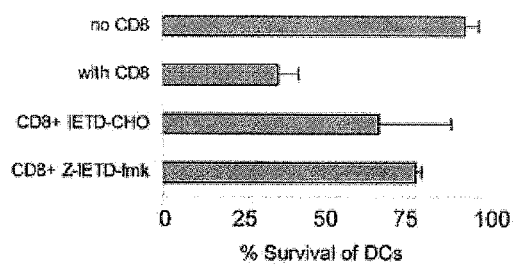
FIGURE 7

A
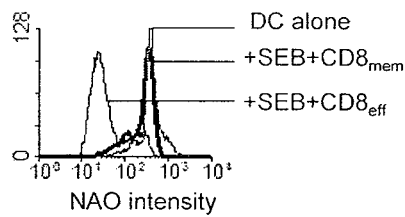
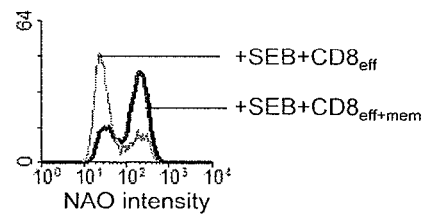
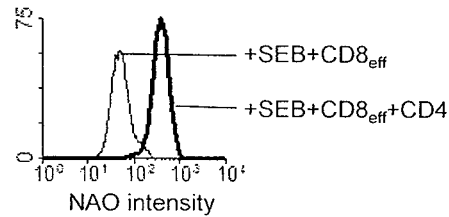
B
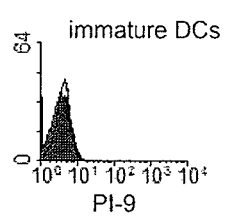
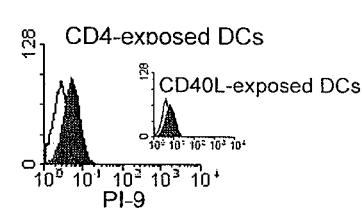
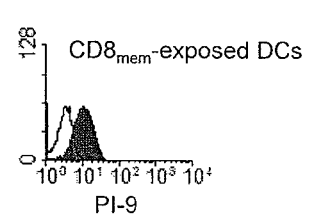
C
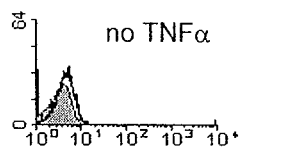
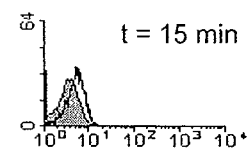
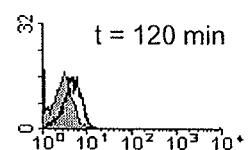
FIGURE 8

VACCINE FOR ACTIVATING HELPER FUNCTION OF CD8+ T CELLS

CROSS-REFERENCE TO RELATED APPLICATIONS

This patent application claims the benefit of U.S. Provisional Patent Application No. 60/891,670, filed Feb. 26, 2007, which is incorporated herein by reference in its entirety.

STATEMENT REGARDING FEDERALLY SPONSORED RESEARCH AND DEVELOPMENT

This invention was made with Government support under Grant Number 1RO1CA95128 awarded by the National Institutes of Health—National Cancer Institute. The Government has certain rights in this invention.

BACKGROUND OF THE INVENTION

Vaccines have long been used for the prevention of infectious diseases, such as viral or microbial infections. The cell-mediated arm of the immune system is extensively involved in providing the host with the ability to defend, recover from infections and to prevent further infections by the same antigen.

Cell-mediated immune mechanisms are also thought to be useful against other diseases such as cancer and autoimmune diseases. Several tumor-related antigens have been identified and used to prepare vaccines intended to treat cancer (e.g., lineage-specific antigens such as MART-1, tyrosinase, gp100, cancer-testis antigens, such as Her2/Neu, CEA, or antigens overexpressed on rapidly proliferating cells, such as cyclins, survivin, etc.). In addition to the defined antigens and their epitopes, whole tumor cells are also used as the source of cancer-relevant antigens.

There is a need for more efficient therapeutic vaccines and improved methods of treatment of cancer and autoimmune diseases.

BRIEF SUMMARY OF THE INVENTION

The invention provides methods of treating or preventing a target disease in a mammal by induction of activated T cells. Use of a non-target antigen to sensitize a patient's CD8+ T cells can be followed with administration of a vaccine comprising a target antigen (such as a tumor-associated antigen or a pathogen-associated antigen) as well as the non-target antigen.

In one aspect, the invention provides a method of treating or preventing a target disease comprising (1) administering a sensitizing composition comprising a non-target antigen to a patient; and (2) administering a therapeutic composition comprising a non-target antigen and a target antigen to the patient, wherein the target antigen is associated with the disease, and wherein the therapeutic composition is administered after the sensitizing compositions, at an interval sufficient for induction of memory T cells.

In another aspect, the invention provides a method of treating or preventing a target disease comprising (1) determining the presence of memory-type immunity to one or more non-target antigens in a patient; and (2) administering a therapeutic composition comprising the non-target antigen and a target antigen to the patient, wherein the target antigen is associated with the disease and wherein the patient was found to have memory-type immunity to the non-target antigen in step (1).

In a further aspect, the invention provides a method of treating or preventing a target disease comprising (1) determining immunity to one or more non-target antigens in a patient; (2) isolating a sample of dendritic cells from the patient; (3) loading the dendritic cells with a target antigen and a non-target antigen, wherein the patient was found to have immunity to the non-target antigen in step (1); and (4) administering to the patient a therapeutic composition comprising the loaded dendritic cells.

In yet another aspect, the invention provides a composition for treating a disease comprising a target antigen, one or more non-target antigens, and a pharmaceutically acceptable carrier.

In another aspect, the invention provides a kit for the treatment of a disease comprising multiple therapeutic compositions, each therapeutic composition comprising a target antigen and one or more non-target antigens.

In yet another aspect, the invention provides a method of treating or preventing a target disease comprising administering a therapeutic composition comprising a target antigen and an inhibitory agent, wherein the target antigen is associated with the target disease, and wherein the inhibitory agent is an agent for preventing the killing of dendritic cell or other antigen-presenting cells, such as an inhibitor of DC apoptosis, an inhibitor of Granzyme B, a Granzyme-B-inducible mediator of apoptosis, an inhibitor of perforin, or a perforin-inducible mediator of apoptosis.

BRIEF DESCRIPTION OF THE SEVERAL VIEWS OF THE DRAWING(S)

FIG. 1(a). $OVA_{257-264}$-specific CD8+ T cells support the induction of CTLs specific for MC38 adenocarcinoma. Mice carrying memory-type $OVA_{257-264}$-specific CD8+ T cell responses, and inoculated with MC38 tumor (day 0), were treated (s.c.; day 3) with DCs loaded with MC38 lysate alone or with $OVA_{257-264}$ as tumor-unrelated heterologous helper epitope. Left: Induction of CTL activity in the spleens of the differentially-treated mice.

FIG. 1(b). Comparison of CTL activity of the splenocytes from the DCs/MC38 lysate/$LCMVgp_{33-41}$-treated mice against the vaccine-relevant (MC38) and irrelevant (EL4) targets. Data from one of two experiments that yielded similar results FIG. 1(c). Memory-type $LCMVgp_{33-41}$-specific CD8+ T cells support the induction of MC38 adenocarcinoma-specific CTLs. Tumor-bearing mice with memory-type $LCMVgp_{33-41}$-specific CD8+ T cell responses were injected (s.c.) with DCs loaded with MC38 tumor lysate, alone or with $LCMVgp_{33-41}$ as a "heterologous" helper epitope. The data from one of three independent experiments that all yielded similar results.

FIG. 1(d). LCMV-specific CD8+ T cells support the induction of CTLs against $OVA_{257-264}$-expressing EG7 lymphoma. Tumor-bearing mice with memory-type $LCMVgp_{33-41}$ specific CD8+ T cell responses were injected (s.c.) with DCs loaded with $OVA_{257-264}$ peptide, as the EG7 tumor-relevant antigen, either alone or with the $LCMVgp_{33-41}$ peptide, as a tumor-unrelated "heterologous" helper epitope. Similar results were obtained in an additional experiment.

FIG. 2(a). MC38-bearing C57BL/6 mice (n=5 mice/group), having naïve CD8+ T cell responses were inoculated with MC38 tumors at day 0 and were treated on day 5, day 9, and day 11 after tumor inoculation.

FIG. 2(b). MC38-bearing C57BL/6 mice (n=5 mice/group), carrying memory-type (week 4) $LCMVgp_{33-41}$-specific CD8+ T cell responses were inoculated with MC38 tumors at day 0 and were treated on day 5, day 9, and day 11 after tumor inoculation.

FIG. 2(c). Memory-type LCMVgp$_{33-41}$-specific CD8+ T cells support the therapeutic activity of vaccination against MC38 adenocarcinoma. Day 3 tumor-bearing mice (n=10 per group) with memory-type responses against tumor-unrelated "heterologous" helper antigens were injected (s.c.) with: PBS as a negative control (open squares), with DCs loaded with tumor antigen alone (MC38 tumor lysate or OVA$_{257-264}$ in the EG7 model), or with the relevant tumor antigen plus a tumor-irrelevant "heterologous" helper epitope (closed circles).

FIG. 2(d). Memory-type OVA$_{257-264}$-specific CD8+ T cells support the therapeutic activity of vaccination against MC38 adenocarcinoma. Day 3 tumor-bearing mice (n=5 per group) with memory-type responses against tumor-unrelated "heterologous" helper antigens were injected (s.c.) with: PBS as a negative control (open squares), with DCs loaded with tumor antigen alone (MC38 tumor lysate or OVA$_{257-264}$ in the EG7 model), or with the relevant tumor antigen plus a tumor-irrelevant "heterologous" helper epitope (closed circles). Data (mean +/−SEM) from one of two separate experiments in each model. The differences between the treatment groups were evaluated using ANOVA: NS: no statistically-significant differences (p>0.05).

FIG. 2(e). Memory-type LCMVgp33-41-specific CD8+ T cells support the therapeutic activity of vaccination against OVA$_{257-264}$-expressing EG7 lymphoma. Day 3 tumor-bearing mice (n=5 per group) with memory-type responses against tumor-unrelated "heterologous" helper antigens were injected (s.c.) with: PBS as a negative control (open squares), with DCs loaded with tumor antigen alone (MC38 tumor lysate or OVA$_{257-264}$ in the EG7 model), or with the relevant tumor antigen plus a tumor-irrelevant "heterologous" helper epitope (closed circles). Data (mean +/−SEM) from one of two separate experiments in each model. The differences between the treatment groups were evaluated using ANOVA: NS: no statistically-significant differences (p>0.05).

Figure 3:
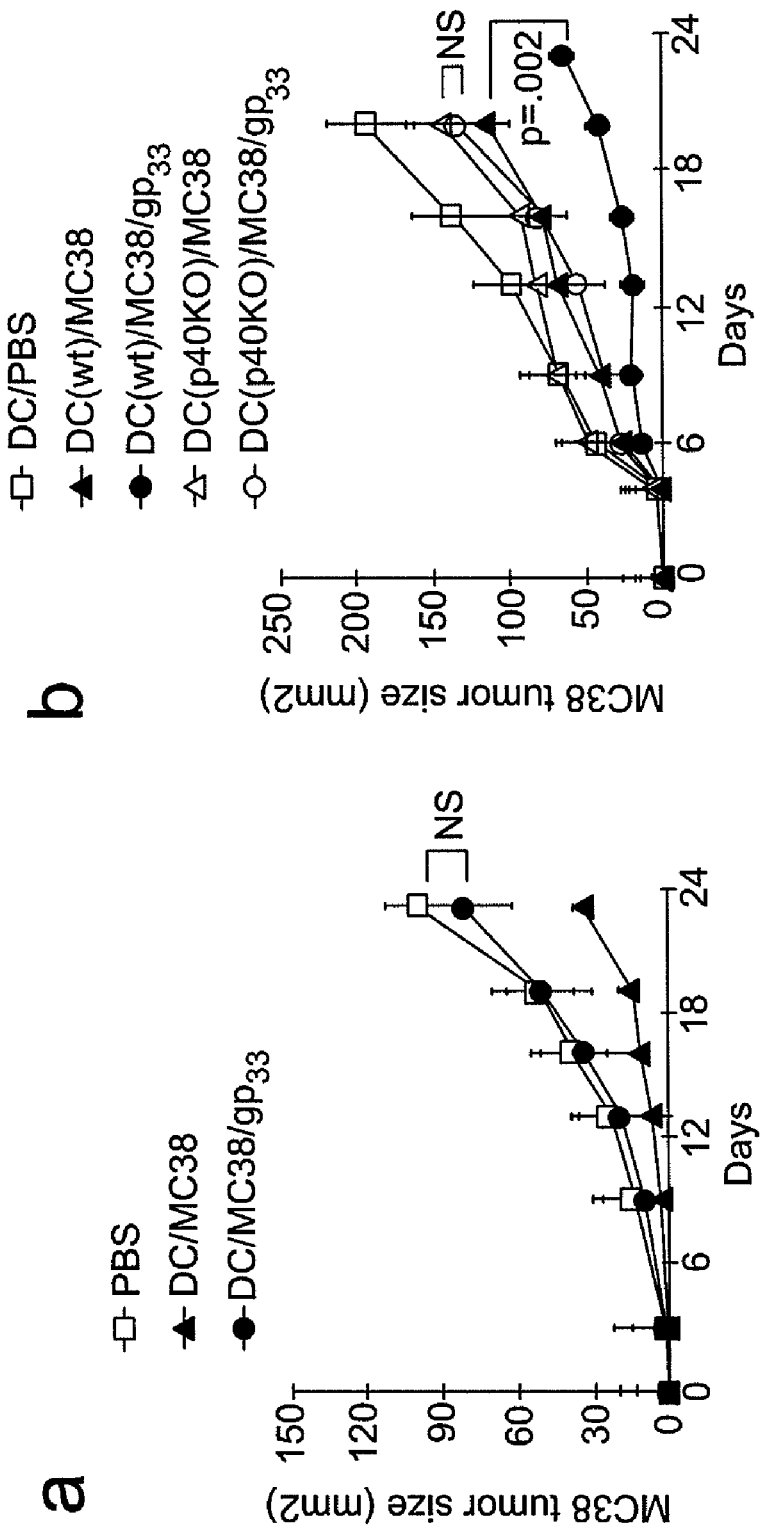

FIG. 3(a). Tumor size in animals with a 1 week-old LCMV-specific response, vaccinated with tumor antigen-loaded DCs (DC/MC38), tumor antigen and LCMVgp$_{33-41}$ antigen-loaded DCs (DC/MC38/gp$_{33}$), and control (PBS). Data (mean +/−SEM from two independent experiments in each model. NS=no statistically significant difference (p>0.05).

FIG. 3(b). Tumor size in animals with a 4 week-old LCMV-specific response, vaccinated with control (DC/PBS), tumor antigen-loaded DCs (DC/MC38), tumor antigen and LCMVgp$_{33-41}$ antigen-loaded DCs (DC/MC38/gp$_{33}$), tumor antigen-loaded p40 knockout DCs (DC(p40KO)/MC38), and tumor antigen and LCMVgp$_{33-41}$ antigen-loaded p40 knockout DCs (DC(p40KO)/MC38/gp$_{33}$). Data (mean +/−SEM from two independent experiments in each model.

Figure 4:
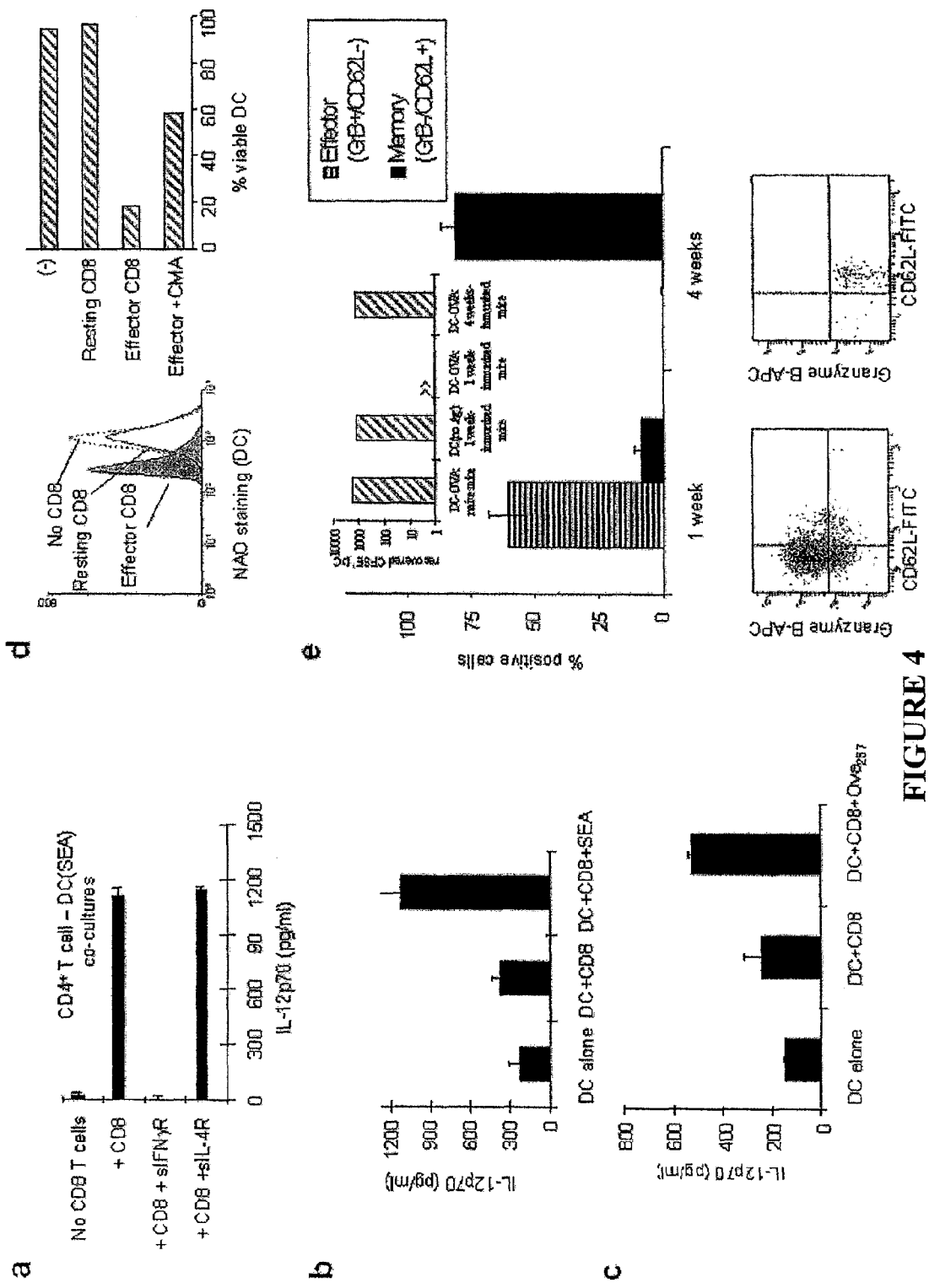

FIG. 4. (a) SEA-coated bone marrow-derived DCs from C57BL/6 mice were co-incubated with syngeneic spleen-isolated CD4+ T cells, either in the absence or in the presence of CD8+ T cells or their combination. Soluble cytokine receptors (IL-4R or IFNγR) were used as indicated to selectively neutralize IFNγ or IL-4, two cytokines with IL-12-enhancing activities. Data (mean +/−SD) from one experiment of three that yielded similar results. (b, c) Interaction with CD8+ T cells primes DCs for high IL-12p70 production. (b) Day 8 DCs were cocultured for 48 h with CD8+ T cells from wild-type B6 mice either in the absence or presence of SEA. (c) DCs were cocultured with H-2 Kb restricted OVA$_{257-264}$-specific CD8+ T cells, freshly isolated from spleens of OT-1 mice, in the presence of OVA$_{257-264}$ peptide. In both cases, after 48 h co-culture, the cells were harvested, washed, and stimulated with CD40L. (d) OVA$_{257-264}$-loaded DC were co-cultured with CD8+ T cells from OT-1 mice, either directly-isolated from OT-1 spleens or OVA257.264-prestimulated for 4 days (respectively Granzyme B$^{low}$/CD62L$^{high}$ resting CD8+ T cells or Granzyme B$^{high}$/CD62L$^{low}$ effector cells; data not shown). The killing of DCs was assessed by mitochondrial damage (reduced NAO staining). Pre-treatment of activated OT-1 cells with CMA was used to inhibit the CTL-dependent DC killing. Similar results were obtained in one additional experiment. (e) Predominance of OVA$_{257-264}$/H-2K$^b$-specific effector versus memory T cells in 1 week-versus 4 week-immunized C57BL/6 mice. Note the predominance of tetramer-positive Granzyme B+/CD62L− effector cells in 1 week-immunized mice, as opposed to selective presence of Granzyme B−/CD62L$^{30}$ memory cells in the spleens of 4 week immunized mice (n=3 mice per group; bottom, representative data from individual animals). The frequencies of tetramer-positive CD8+T cells in 1 week-and 4 week-immunized mice were 4.3% (+/−1.5) and 0.7% (+/−0.3), respectively. Data from one of two experiments that yielded similar results. Inset: Selective elimination of OVA$_{257-264}$- carrying CFSE-labeled DCs in 1-week-immunized, but not 4 week-immunized, mice. Naïve mice and 1-week-preimmunized mice receiving sham-loaded DCs served as control groups.6 Mice (3 mice/group) were injected with 10$^6$ DC and draining lymph nodes were removed after 16h.

FIG. 5. (A(1)) Tissue-derived effector CD8+ T cells eliminate DCs, as indicated by decrease in NAO staining intensity, demonstrating the loss of mitochondrial integrity. (A(2)) Blood-isolated memory CD8+ T cells do not kill DCs as reflected by the maintained NAO staining pattern of the DCs. (B(1)) DC activation status was determined by flow cytometric analysis for surface expression of the co-stimulatory molecule CD86 and DC maturation associated marker CD83. All data is gated on DCs, based on forward- and side-scatter profiles. (B(2)) IL-12p70 production by DCs following stimulation with J588-CD40L, as measured by ELISA. Results (mean +/−SD or triplicate cultures) are representative of three independent experiments.

FIG. 6-I. (A(1), B(1)) In vitro generated Granzyme B$^{hi}$/perforin$^{hi}$ effector-type CD8+ T cells and activated gp100-specific CD8+ T cells kill DCs as evident from decrease in NAO staining intensity. (A(2), B(2)) In vitro generated Granzyme Blo/perforinlo memory-type CD8+ T cells and resting gp100-specific CD8+ T cells do not kill immature DCs as reflected by the maintained NAO staining pattern of the DCs.

FIG. 6. DC-killing versus DC-activating functions of in vitro generated effector-type CD8+T cells and memory-type CD8+ T cells at different stages of activation. Interaction of DCs with the in vitro generated effector (left)-or memory (right)-type CD8+ T cells (A, C) or with melanoma (gp 100)-specific CD8+T cells (B, D), at early or late stages of activation. (A, B) Left: in vitro generated Granzyme B$^{hi}$/perforin$^{hi}$ effector-type CD8+ T cells and activated gp 100-specific CD8+T cells kill DCs as evident from decrease in NAO staining intensity. Right: in vitro generated Granzyme Blo/perforinlo memory-type CD8+ T cells and resting gp l00-specific CD8+T cells do not kill immature DCs as reflected by the maintained NAO staining pattern of the DCs. (C, D) Memory-type CD8+ T cells at later stage of activation and resting melanoma (gp 100) specific CD8+ T cells induce DC maturation and prime DC for enhanced IL-12 production. Day 6, immature HLA-A2+DCs were co-cultured with melanoma gp 100-specific HLA-A2 restricted CD8+T cells, in the presence of gp 100 (209-217) peptide (shaded histograms). Memory-type CD8+ T cells were co-cultured with SEB loaded DCs for 48 hours. Left: Activation status of DCs (CD86, CD83) was assessed by flow cytometry (data gated on DCs). Right: IL-12p70 was measured in supernatants after stimulation of DCs with J588-CD40L. DC killing and DC activation required the presence of antigen in all the above systems (not shown).

FIG. 7. (A)(1): The survival of DCs was analyzed by change in the light scatter properties (as indicated by dot plots: left). (A)(2): Survival of DCs was verified using the NAO staining. Broken line within the dot plot separates live and dead cell populations. NAO analysis included both regions (live and dead DCs) while the CD8$^+$ T cell population was excluded. (B): CMA-treated (perforin-blocked) effector-type CD8$^+$ T cells enhance DC activation. TNFα (50 ng/ml) induced DC maturation was used as positive control. (C): CMA-treated (perforin-blocked) effector-type CD8$^+$ T cells induce type-1 polarized phenotype in DCs, characterized by enhanced ability to produce IL-12p70. *: below detection limit. Results are representative of three independent experiments. (D): Dendritic cells pretreated (1 hour) with IETD-CHO (200 μM) or Z-IETD-fmk (20 μM), were co-cultured with effector-type CD8$^+$ T cells. Survival of DCs was analyzed after 10-12 hours. The data from two experiments are expressed as percent survival of DCs (mean +/−SEM).

FIG. 8. Memory-type CD8$^+$ T cells and CD4$^+$ T cells induce DC expression of endogenous Granzyme B inhibitor and protect DCs from CTL mediated killing. (A) Exposure of DCs to memory-type CD8$^+$ T cells confers protection from effector-type CD8$^+$ T cell mediated death, analogous to CD4$^+$ T cell mediated protection. Memory CD8$^+$ T cells or CD4$^+$ Th cells were co-cultured with SEB-loaded DCs for 8-10 hours, followed by the addition of effector CD8$^+$ T cells. DC viability was assessed by NAO staining at 24 hours. (B) Memory-type CD8$^+$ T cells induce uniform DCs expression of the endogenous Granzyme B inhibitor: PI-9 (10 hour co-culture). DCs exposed to memory-type CD8$^+$ T cells, CD4$^+$ T cells (or CD40L: see the inset) were stained for intracellular PI-9. (C) Rapid induction of PI-9 in DCs exposed to TNFα. Intracellular expression of PI-9 (open profiles) in DCs analyzed by flow cytometry before and after (15 and 120 minutes) the exposure to recombinant TNFα (50 ng/ml).

Figure 9:
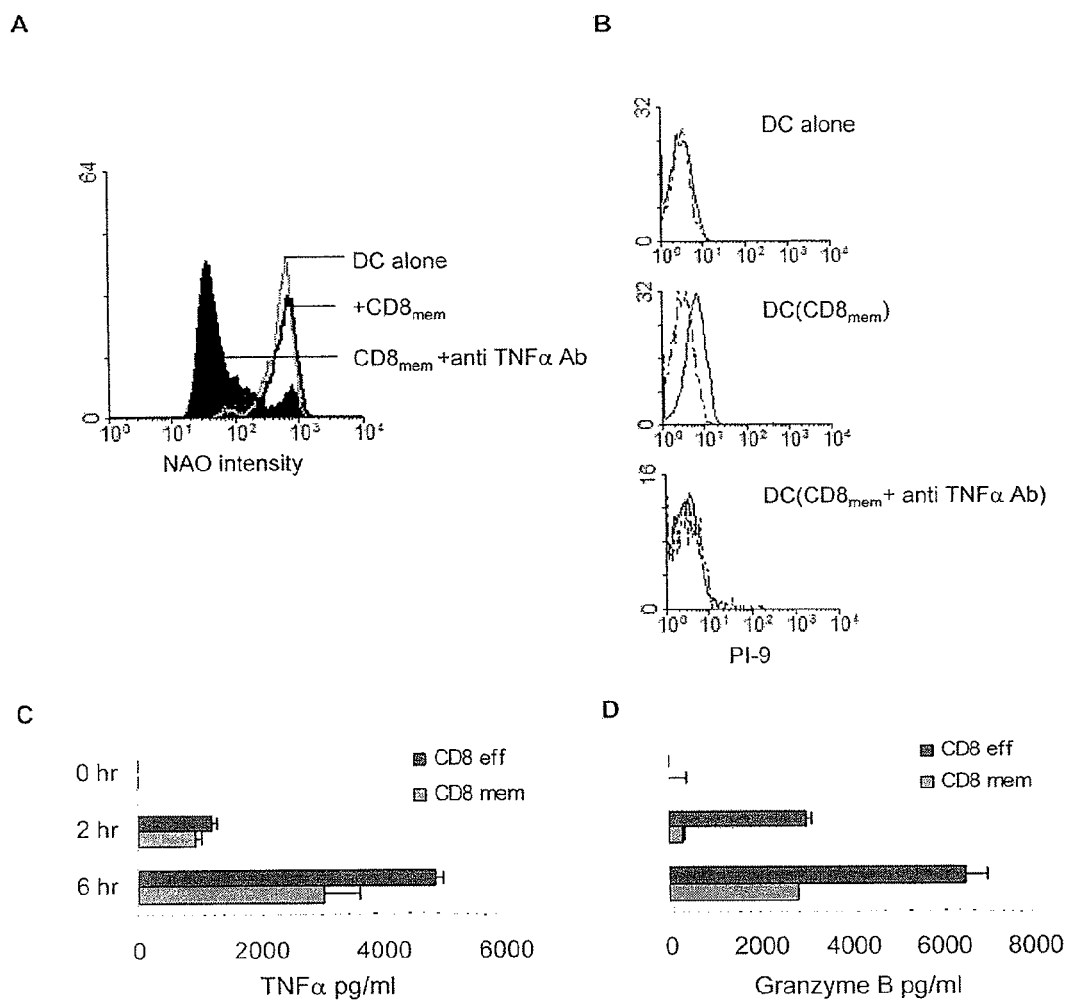

FIG. 9. Memory-type CD8$^+$ T cell-derived TNFα plays a crucial role in helper function. (A) Neutralization of TNFα in the co-cultures of SEB-loaded DCs and memory-type CD8$^+$ T cells using anti-TNFα antibody, reduces DC survival (24 hour cultures). (B) anti-TNFα antibody, blocks the memory-type CD8$^+$ T cell-induced induction of PI-9 in DCs (10 hour time point). (C) Exogenous TNFα protects immature DCs from CTL-mediated killing. Immature DCs were pre-treated with rhuTNFα (100 ng/ml; 24 hours) prior to co-cultures with effector CD8$^+$ T cells. (D) Different relative kinetics of the TNFα versus Granzyme B release in memory and effector CD8$^+$ T cells during the interaction with DCs.

Figure 10:
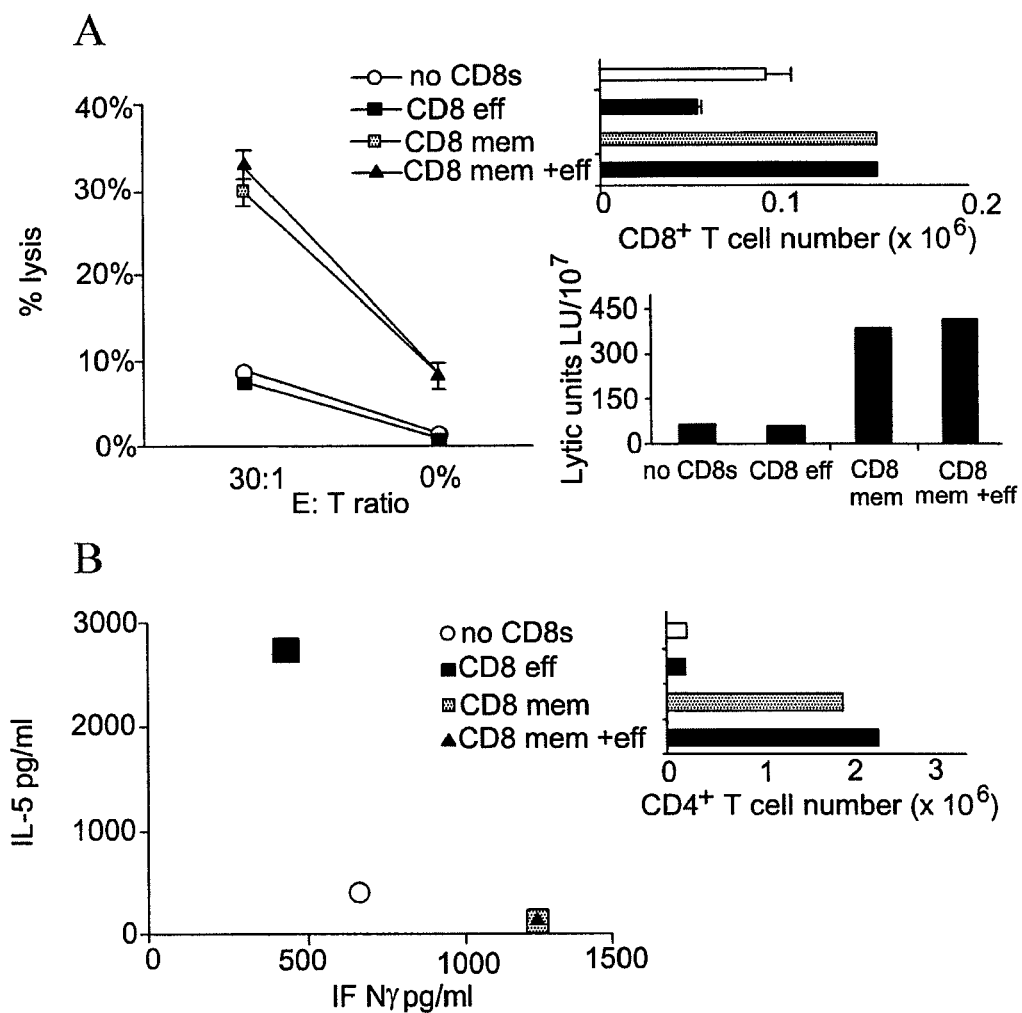

FIG. 10. Memory CD8$^+$ T cells support de novo induction of functional CTLs and Th1 cells. (A-B) Memory and effector CD8$^+$ T cells have reciprocal impact on the DC-driven expansion of CTL- and Th1 cell progenitors and the development of CTL and Th1 functions. Blood-isolated naive CD8$^+$ or CD4$^+$ T cells were primed with the SEB-loaded immature DCs in the absence or presence of a-irradiated memory-type or effector-type CD8$^+$ T cells. The expanding cultures of naive CD8$^+$ or CD4$^+$ T cells were harvested, respectively at day 5 or day 10, counted and tested for their functional activity, using CTL assay or the analysis of their Th1/Th2 cytokine profiles. (A) Memory CD8$^+$ T cells support the expansion of CTL precursors and their acquisition of functional activity. Left: CTL activity of CD8$^+$ T cell cultures performed in the presence or absence of memory or effector CD8$^+$ T cells was assessed by 51Cr release assay, using SEB-loaded JY-1 cells as targets. Data from one of two independent experiments, that both yielded similar results. (B) Memory CD8$^+$ T cells support the expansion of Th1 cell precursors and the acquisition of Th1 cytokine production profiles. Right: Ability of memory-type CD8$^+$ T cells, but not effector-type CD8$^+$ T cells, to induce naive CD4$^+$ T cell proliferation. Left: $^{naive}$ CD4$^+$ T cells primed in the presence of memory-type CD8$^+$ T cells develop a strongly polarized Th1 cytokine profile as determined by ELISA. Data from one of two independent experiments, that both yielded similar results.

DETAILED DESCRIPTION OF THE INVENTION

The invention provides methods and compositions for the treatment or prevention of a disease in a patient by the induction of memory T cells, using a combination of a target antigen (such as a tumor-associated antigen or a pathogen-associated antigen) and a non-target antigen. Without being bound by any particular theory, it is thought that CD8$^+$ memory T cells to a non-target antigen can support dendritic cells (DC) in activating additional naive CD8$^+$ T cells against a target antigen, thereby increasing cytotoxic T lymphocyte (CTL) activity against cells having the target antigen, such as tumor cells or cells infected with a pathogen.

In some embodiments, the invention provides a method of treating or preventing a target disease comprising (1) administering a sensitizing composition comprising a non-target antigen to a patient; and (2) administering a therapeutic composition comprising a non-target antigen and a target antigen to the patient, wherein the target antigen is associated with the disease, and wherein the therapeutic composition is administered after the sensitizing compositions, at an interval sufficient for induction of memory T cells.

The interval required for induction of memory T cells can be evaluated using standard methods known to one of ordinary skill in the art and described herein. For example, the levels of CD62L or CCR7 can be detected using flow cytometry assays (Sallusto et al., *Annu Rev Immunol* 22: 745-763 (2004); Lanzavecchia et al., *Science* 290:92-97 (2000). Observation of CD62L(high) or CD45R0(high)/CD62L (high) phenotype on the expanded population of antigen specific CD8$^+$ T cells compared to the effector stage where CD62L (negative/low cells predominate can indicate that memory T cell activity has been induced. Additionally or alternatively, high expression of a surface marker CCR7 (see, e.g., Rivino et al., *J. Exp. Med.* 200:725-735 (2004)) or low levels of intracellular marker Granzyme B in the expanded antigen-specific population can be used to identify the memory cells with functional helper function (see, e.g., FIG. 4 and Nakamura et al., *Cancer Res* 67:10012-10018 (2007) at FIG. 1). Although naïve cells express similar to memory cells CD62L (high), CCR7 (high), and Grenzyme B (low)phenotype, in contrast to memory cells they are not expanded (low frequencies) and do not express CD45R0 marker, instead expressing CD45RA (Lanzavecchia et al., *Nat Rev Immunol* 2: 982-987 (2002)). In other embodiments, one of ordinary skill in the art may simply employ a pre-determined interval between administration of the sensitizing composition and a therapeutic composition. For example, an interval of 4 weeks, 5 weeks, 6 weeks, or more than 6 weeks may separate administration of compositions comprising a particular non-target antigen. It will be understood that in some patients and/or in the use of different non-target antigens, a shorter or longer interval may be advantageous.

The sensitizing composition can comprise one or more non-target antigens. Preferably, the non-target antigen of the sensitizing composition is the same as the non-target antigen of the therapeutic composition. In some embodiments, the sensitizing composition comprises multiple non-target antigens, and the therapeutic composition comprises at least one of the non-target antigens present in the sensitizing composition. In other embodiments, the sensitizing composition comprises multiple non-target antigens, and the therapeutic composition also comprises multiple non-target antigens. The sensitizing composition and/or the therapeutic composition can comprise 1, 2, 3, 4, 5, 6, 7, 8, 9, 10, 15, 20, or more than 20 non-target antigens.

The non-target antigen can be any suitable epitope against which $CD8^+$ T cells can be safely and desirably be induced. The non-target antigen can be viral, bacterial, protozoan, helminthic, mycobacterial, alloantigen, or xenoantigen. In a preferred embodiment, the epitope can be from a viral source, such as hepatitis Herpes simplex, CMV, EBV and other herpes viruses, HBV and HCV, and influenza virus. Any suitable non-target antigen or combination thereof can be used, although it will be understood that commercially available compositions, such as influenza vaccines, will be particularly useful in the methods of the present invention.

The target disease can be any disease such as cancer or an infectious disease. In one preferred embodiment, the disease is cancer. The cancer can be of any organ or tissue, including but not limited to solid organ tumors. For example, the cancer can be melanoma, colon-, breast-, lung, cervical-, ovarian, endometrial-, prostate-, skin-, brain-, liver-, kidney, thyroid, pancreatic, esophageal-, or gastric cancer, leukemias, lymphomas, multiple myeloma, myelodysplastic syndrome, pre-malignant HPV-related lesions, intestinal polyps and other chronic states associated with increased cancer risk. It will be understood that known or later discovered cancer-associated antigens can be used in the compositions and methods of the present invention as target antigens for treating cancer.

In another embodiment, the target disease is an infectious disease. The infectious disease can have a viral, bacterial, protozoan, parasitic, or other pathogenic origin. In some preferred embodiments, the disease can be primarily caused by or secondary to infections such as HIV, hepatitis B, hepatitis C, cytomegalovirus (CMV), Epstein-Barr virus (EBV), Pox virus, influenza including avian flu, severe acute respiratory syndrome (SARS), mycobacterial infections including tuberculosis and leprosy, leishmaniasis, malaria, anthrax and other bioterrorism agents. It will be understood that known or later discovered pathogen-associated antigens can be used in the compositions and methods of the present invention as target antigens for treating infectious diseases.

The patient can be a human or any suitable non-human mammal such as a mouse, rat, rabbit, cat, dog, pig, sheep, cow, or primate. In some embodiments, the patient is a non-human experimental animal model. In a preferred embodiment, the patient a primate. In a more preferred embodiment, the patient is a human.

In some embodiments, the method can further include the step of administering one or more additional therapeutic compositions each comprising the target antigen and a non-target antigen. In such embodiments, each non-target antigen or combination thereof can be distinct, i.e., although each therapeutic composition comprises a common target antigen and one or more non-target antigens, no therapeutic composition comprises the same non-target antigen(s) present in any other therapeutic composition. In a preferred embodiment, multiple therapeutic compositions are administered cyclically, i.e., no single therapeutic composition is administered consecutively.

The invention further provides a method of treating or preventing a target disease comprising (1) determining the presence of memory-type immunity to one or more non-target antigens in a patient; and (2) administering a therapeutic composition comprising the non-target antigen and a target antigen to the patient, wherein the target antigen is associated with the disease and wherein the patient was found to have memory-type immunity to the non-target antigen in step (1).

The presence of memory-type immunity to one or more non-target antigens can be determined, as described above, by any method known to one of ordinary skill in the art, such as by determining CD62L levels or DC killing capacity.

In some embodiments, the method can further comprise the step of administering to the patient one or more additional therapeutic compositions as described above, comprising the target antigen and a non-target antigen, wherein the patient was determined to have immunity to the each non-target antigen in step (1).

Where memory-type immunity to a non-target antigen is determined prior to administration of a therapeutic compound, a sensitizing composition is not necessarily employed, but if a sensitizing composition is to be administered, it can include any suitable non-target antigen or combination thereof as described above.

Additionally, the invention provides a method of treating or preventing a target disease comprising (1) determining immunity to one or more non-target antigens in a patient; (2) isolating a sample of dendritic cells from the patient; (3) loading the dendritic cells with a target antigen and a non-target antigen, wherein the patient was found to have immunity to the non-target antigen in step (1); and (4) administering to the patient a therapeutic composition comprising the loaded dendritic cells.

In some embodiments, the method can further comprise the step of administering to the patient one or more additional therapeutic compositions comprising dendritic cells loaded with the target antigen and a non-target antigen, wherein the patient was determined to have immunity to each non-target antigen in step (1).

The invention further provides a composition for treating a target disease comprising a target antigen, one or more non-target antigens, and a pharmaceutically acceptable carrier.

The target disease, target antigen and/or non-target antigen can be as described above. In some embodiments, one or more of the antigens are covalently linked. Preferably, a target antigen is linked to a non-target antigen.

In yet another embodiment, the invention provides a method of treating or preventing a target disease comprising administering a therapeutic composition comprising a target antigen and an inhibitory agent. The inhibitory agent can be any agent useful for converting suppressor activity of effector cells into helper cells. Without being bound by any particular theory, it is thought that such a combination can prevent the killing of dendritic cells or other antigen-presenting cells. In some embodiments, the inhibitory agent(s) can be inhibitors of DC apoptosis, inhibitors of Granzyme B, Granzyme-B-inducible mediators of apoptosis, inhibitors of perforin, and perforin-inducible mediators of apoptosis. (see, e.g., Maczek et al., *Int J Cancer* 115: 450-455 (2005); Semenzato et al., *Cancer* 48: 2191-2197 (1981); Tsukishiro et al., *Cancer Immunol Immunother* 52: 599-607 (2003)).

In some embodiments, the inhibitor is covalently linked to the antigen. The inhibitory agent and antigenic determinant can be linked directly, by a linker sequence, or any form of a carrier molecule. In a preferred embodiment, the inhibitor and the target antigen are linked together and linked to additional molecules facilitating their entry into cells. The inhibitory agent can optionally be linked to the target antigen and/or to additional molecule(s), such as molecules capable of facilitating entry into cells.

The compositions of the present invention can be prepared in any useful pharmaceutical formulation known to one of ordinary skill in the art. It will be understood that in many embodiments, the compositions will be in liquid form. The liquid compositions of the invention, whether they be solutions, suspensions or other like form, can include one or more of the following components: sterile diluents such as water for injection, saline solution, preferably physiological saline, Ringer's solution, isotonic sodium chloride, fixed oils such as synthetic mono or diglycerides which can serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred diluent. An injectable pharmaceutical composition is preferably sterile.

The pharmaceutical compositions can be prepared by methodology well known in the pharmaceutical art. The antigens of the invention can be in the form of a solvate in a pharmaceutically acceptable solvent such as water or physiological saline. Alternatively, the compounds can be in the form of the free base or in the form of a pharmaceutically acceptable salt such as the hydrochloride, sulfate, phosphate, citrate, fumarate, methanesulfonate, acetate, tartrate, maleate, lactate, mandelate, salicylate, succinate and other salts known in the art. The appropriate salt would be chosen to enhance bioavailability or stability of the compound for the appropriate mode of employment (e.g., oral or parenteral routes of administration).

Dendritic cells used as live vaccines can be injected in saline, phosphate buffer, or other cell media supporting their viability. In some embodiments, the media can be supplemented with human plasma, human serum, or human serum albumin.

A composition formulated to be administered by injection can be prepared by combining the agonist with water, and preferably buffering agents, so as to form a solution. The water is preferably sterile pyrogen-free water. A surfactant can be added to facilitate the formation of a homogeneous solution or suspension. Surfactants are compounds that facilitate dissolution or homogeneous suspension of the agonist in the aqueous delivery system. Other carriers for injection include, without limitation, sterile peroxide-free ethyl oleate, dehydrated alcohols, propylene glycol, as well as mixtures thereof.

Suitable pharmaceutical excipients for the injecting solutions include stabilizing agents, solubilizing agents, buffers, and viscosity regulators. Examples of these adjuvants include ethanol, ethylenediaminetetraacetic acid (EDTA), tartrate buffers, citrate buffers, and high molecular weight polyethylene oxide viscosity regulators. These pharmaceutical formulations can be injected intramuscularly, epidurally, intraperitoneally, or intravenously.

The invention also provides a kit for the treatment of a target disease comprising multiple therapeutic compositions as described above, each therapeutic composition comprising a target antigen and one or more non-target antigens.

The following examples further illustrate the invention but, of course, should not be construed as in any way limiting its scope.

EXAMPLE 1

This example demonstrates that memory $CD8^+$ T cells support the DC mediated induction of tumor-specific cytotoxic T lymphocyte (CTL) responses.

The therapeutic activity of dendritic cells ("DCs") loaded with tumor-relevant antigens, alone or with tumor-unrelated "heterologous" class I-restricted peptide epitopes (LCMVgp33-41 peptide or $OVA_{257-264}$ peptide), was tested against the established (day 3-5) MC38 and EG7 tumors in wild-type C57BL/6 mice harboring memory-type $CD8^+$ T cells against defined MHC class I-restricted epitopes of OVA or LCMV.

Mice. Female 6-8-week-old C57BL/6, C57BL/6Tg (TcraTcrb)1100Mjb (OT-1), and C57BL/6-IL12tm1Jm (IL-12p40 knockout), female mice purchased from Jackson Laboratories (Bar Harbor, Me.) were maintained in microisolator cages and used for all experiments at 8-10 weeks of age.

Cell Lines, Isolation, and Culture. MC38 adenocarcinoma was provided by Dr. D. L. Bartlett, University of Pittsburgh (originally from Dr. S. A. Rosenberg, NCI). EL4 and EG7 (OVA-expressing EL4) cell lines were purchased from ATCC (Manassas, Va.). Spleen $CD4^+$ and $CD8^+$ T cells were negatively selected using StemSep™ isolation columns (Stem Cell Technologies, Vancouver, BC) with 90-95% purity. In some in vitro experiments (FIG. 1c), additional anti-LyC6-mediated removal 26 of preactivated OT-1 cells was performed. All cells were maintained in complete medium (CM): RPMI 1640 with 10% heat-inactivated fetal bovine serum (Invitrogen, Carlsbad, Calif.), glutamine, streptomycin and penicillin (Invitrogen).

Dendritic Cells. Bone marrow-derived DCs were generated in GM-CSF and IL-4 (both 1000 U/ml; Schering-Plough, Kenilworth, N.J.)-supplemented cultures, as described 27. On day 6-7, $CD11c^+$ DCs were isolated using anti-mouse CD11c-coated magnetic beads (Miltenyi Biotech.) and MACS™ separation columns. DCs expressed CD11c, CD40, CD80, CD86, and MHC class I and class II antigens (Son et al., *J Immunol Methods* 262: 145-57 (2002) and data not shown).

Induction of LCMV- or OVA-specific immune responses. LCMVgp33-41 peptide, (KAVYNFATC), the dominant H2-Db/Kb-restricted epitope of LCMV, and dominant H-2 Kb restricted OVA epitope, $OVA_{257-264}$ (SIINFEKL), were synthesized by the University of Pittsburgh Peptide Synthesis Facility. Peptide-loaded DCs were washed twice and injected s.c. ($3 \times 10^5$ DCs in 0.2 ml of PBS) twice with 1-week interval. The presence of effector and memory $CD8^+$ T cells in the spleens and lymph nodes of vaccinated animals was determined by 3-color flow cytometry after staining of isolated $CD8^+$ T cells, with CD62L (MEL-14; BD-Pharmingen), Granzyme B (GB121; CalTag), and tetramer (iTAg™, Beckman-Coulter, Fullerton, Calif.).

DC elimination in vivo. DCs ($OVA_{257-264}$- or PBS-loaded; $1 \times 10^6$) were labeled with CSFE (1 µM for 10 min at 37° C.), washed 3 times and injected into the footpads. After 24 h, single cell suspensions from popliteal lymph nodes were prepared and analyzed by flow cytometry. Total node cellularity was counted in hemocytometer.

Tumor vaccines. DCs were loaded overnight with MC38 tumor cells lysates (three freeze-thaw cycles; centrifuged, and supernatant collected), at three tumor cell equivalents to one DC, in the presence of LPS. DCs were resuspended in RPMI 1640 and loaded, with $OVA_{257-264}$, LCMV $gp_{33-41}$, or PBS. For preparation of the EG7 vaccine, DCs were loaded with $OVA_{257-264}$ (alone or with LCMV gP33-41). All vaccines were washed twice and suspended in PBS.

Tumor therapy models. Wild-type C57BL/6 mice (7-12/ group; including 2 animals/group for CTL assays), naive or carrying week-1 or week-4 immune responses against LCMV or OVA, were inoculated (right flank; s.c.; day 0) with high numbers of tumor cells ($3 \times 10^5$ MC38 or $3 \times 10^6$ EG7), to induce rapid tumor growth that was only marginally sensitive to standard therapeutic vaccines (see FIG. 3). The mice were vaccinated ($3 \times 10^5$ DCs, on the distant site on same flank, s.c. on day 3, or on days 5.9-11, as indicated). Tumors were measured by vernier calipers every 3-4 days. Data are reported as the mean $^+$/$-$SEM of tumor area (product of the largest perpendicular diameters).

CTL activity. 10 days after vaccination, splenocytes were harvested from two (tumor-bearing) mice per group. They were restimulated in vitro ($1 \times 10^6$ cells/well) with $1 \times 10^5$ gamma-irradiated (10,000 R) MC38 or EG7 cells in the presence of 30 IU/ml rhuIL-2 in 24-well culture plates. Lymphocytes were harvested after 5 days and used in 5 h 51 Cr release assays against MC38 and EG7 targets, with EL4 cells used as non-specific controls.

Statistical analysis. Data collected beyond day 4 until the last day of tumor area measurement were (natural) log transformed and used to fit a parametric mixed linear model that included animals as random effects with treatment group and day of measurement as fixed effects. If either group differences or group by time interaction were significant at p<0.05 the analysis was applied to the last day of tumor area measurement. Data were (natural) log transformed when appropriate and a one way parametric analysis of variance (ANOVA) was used as an omnibus test of differences. Unless tests were significant at level $\alpha$=0.05, no further testing of specific contrasts was conducted. Otherwise, individual pair-wise comparisons were conducted with the t test (after data transformation). All tests were two tailed.

Results. The "heterologous" OVA and LCMV helper epitopes were only present in cancer vaccines and were not expressed by the tumor itself. Therefore, any "helper" or "suppressor" impact of ($OVA_{257-264}$-specific or $LCMVgp_{33-41}$-specific) $CD8^+$ T cells on the development of the immune responses against MC38 or EG7 tumors, could be analyzed in isolation from a possible indirect modulatory impact of $CD8^+$ T cells, mediated by tumor antigens and other tumor-derived factors differentially released from the CTL-targeted tumor tissues. As shown in FIGS. 1(a)-(c), the inclusion of the non-tumor antigens in the autologous DC cancer vaccine loaded with the relatively poorly immunogenic MC38 tumor lysate supported the generation of MC38-specific CTL responses in wild-type C57BL/6 animals. Use of $OVA_{257-264}$ (FIG. 1c) and use of $LCMVgp_{33-41}$ (FIG. 1d) in combination with the MC38 tumor antigen was more effective in killing MC38 than a DC vaccine loaded only with tumor antigen, which was similar in effect to the PBS negative control.

The vaccines including the LCMVgp33-41 CD8 helper epitope not only showed strongly elevated CTL-inducing function against the poorly-immunogenic MC38 adenocarcinoma, but also further enhanced the CTL responses against the highly-immunogenic (OVA-expressing) EG7 lymphoma, induced by $OVA_{257-264}$-loaded DCs (FIG. 1d).

These results confirm that the ability of the $CD8^+$ T cells specific for an individual epitope ($OVA_{257-264}$), to provide CD8 helper signals (FIG. 1a-b) and to benefit from such signals (FIG. 1d) indicates that $CD8^+$ T cell help is not restricted to responses against some unique antigens (e.g. responses to "strong" immunogens facilitating the responses to "weak" immunogens), but that naive $CD8^+$ T cells can become memory cells and provide helper signals to other cells.

EXAMPLE 2

This example demonstrates the enhancement in therapeutic effect in vivo when memory T cells are activated against a heterologous epitope.

Tumor vaccines as described above were applied in the tumor therapy model described above against established (day 3-5) MC38 and EG7 tumors in wild-type C57BL/6 mice. Mice were LCMV naïve, or carrying memory-type (4 week) LCMV-specific $CD8^+$ T cells or carrying effector-type (1 week) LCMV-specific response. All mice were monitored for tumor growth.

As shown in FIG. 2a, DCs loaded with tumor material alone had only marginal impact on the growth of established MC38 tumors. In LCMV-naive mice, this outcome of was not improved by the inclusion of the $LCMVgp_{33-41}$ "helper" epitope in the vaccines (FIG. 2a). However, in mice harboring memory-type responses against the MHC class I-restricted $LCMVgp_{33-41}$ epitope, the vaccination with DCs loaded with MC38 tumor lysate and $LCMVgp_{33-41}$, the "heterologous CD8 helper" peptide, resulted in a distinct therapeutic effect against day 5 established tumors that were resistant to treatment with standard DC-based vaccines (FIG. 2b). These beneficial effects of "heterologous CD8 help" were not seen after vaccination with DCs loaded with $LCMVgp_{33-41}$ alone.

Figure 2:
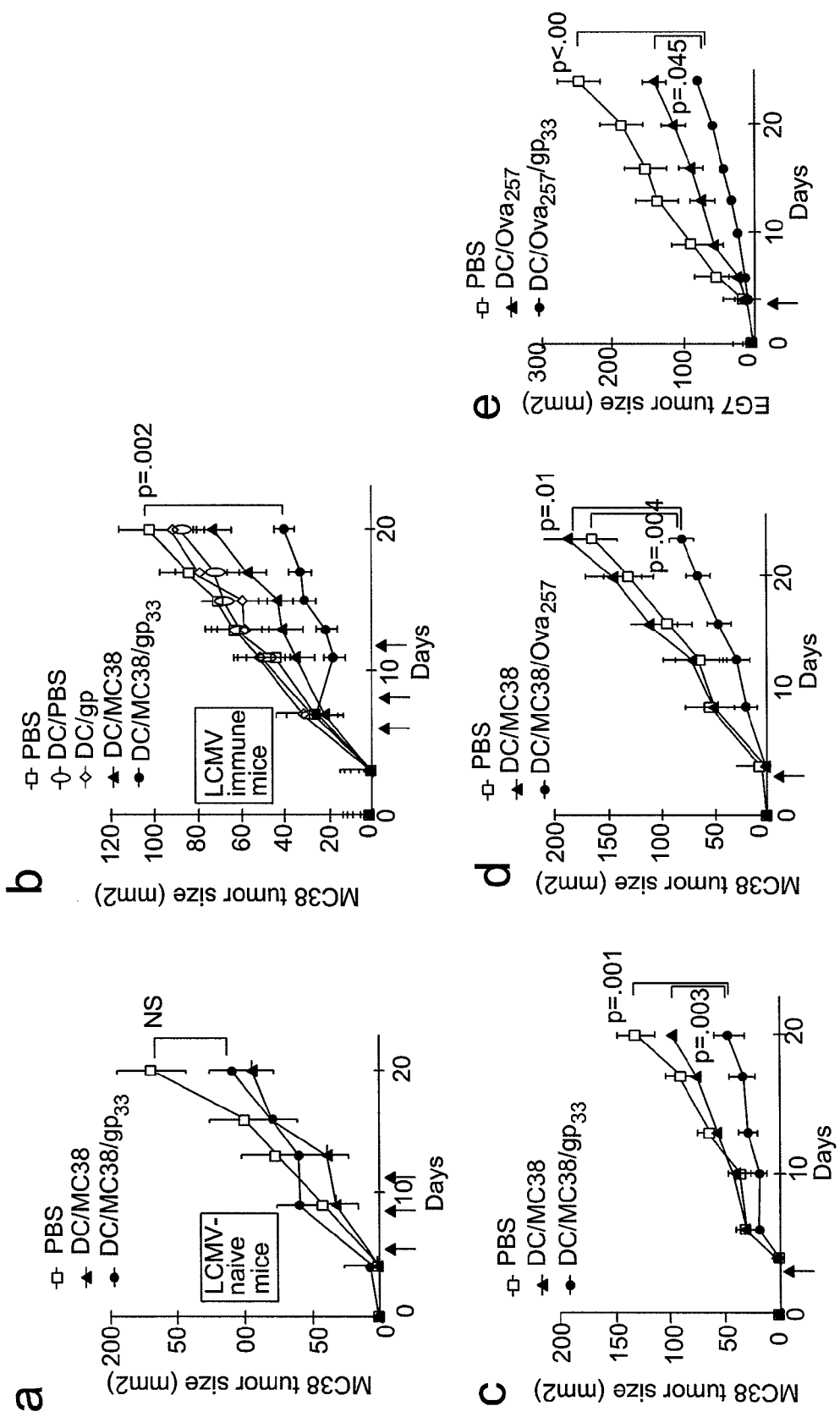

The positive effects of inclusion of $LCMVgp_{33-41}$ peptides on enhancement of the memory $CD8^+$ T cell response as shown in FIGS. 1-2 were eliminated in animals pre-immunized with LCMV at 1 week prior to tumor inoculation (FIG. 3a). No significant difference was found in tumor size between MC38/$LCMVgp_{33-41}$ vaccination and the PBS control.

Similar enhancement of the therapeutic efficacy of vaccination has been observed in three additional models, when using $LCMVgp_{33-41}$ or $OVA_{257-264}$ to enhance the antitumor effects of a single (rather than triple) dose of vaccine against the 3 day old MC38 tumors (FIGS. 2c, d), or when using $LCMVgp_{3341}$ to boost the antitumor effects of vaccination against significantly more immunogenic EG7 lymphoma (FIG. 2e). The results of these functional tests of anti-tumor activity demonstrated that $OVA_{257-264}$-specific $CD8^+$ T cells at their naive stage can benefit from "helper" signals delivered by memory T cells (in the current experiments: specific for $LCMVgp_{33-41}$), but at the memory stage they can themselves act as a source of $CD8^+$ T cell helper signals, verifying that the ability to receive and provide "CD8 helper" signals is a general feature of $CD8^+$ T cells.

These results confirm that the reduction in tumor growth is due to not due to nonspecific immunostimulatory effects of activation of high numbers of LCMV-specific $CD8^+$ T cells present in these animals, but rather that "helper" signals from memory $CD8^+$ T cells can enhance the therapeutic activity of vaccination against established tumors.

EXAMPLE 3

This example demonstrates the role of IL-12-producing DCs in mediating "CD8 help."

DC tumor vaccines were prepared as described above using wild-type DCs as above or DCs generated from the bone marrow of p40 knockout mice. (see, e.g., Nakamura et al., *Cancer Res* 67: 10012-10018 (2007); Schijns et al., *J Immunol* 160: 3958-3964 (1998); Mattner et al., *Eur J Immunol* 26: 1553-1559 (1996)). The vaccines were administered in the tumor therapy model as described above.

In further support of the central role of DCs and the DC-produced IL-12, the "heterologous help" from memory-type $CD8^+$ T cells could not be mediated by IL-12-deficient DCs generated from the bone marrow of p40-knockout animals (FIG. 3b).

EXAMPLE 4

This example demonstrates the ability of human memory $CD8^+$ T cells to regulate survival and functions of dendritic cells as compared to human effector $CD8^+$ T cells.

Media, reagents, and cell lines. The cell cultures were performed using either IMDM (Invitrogen, Carlsbad, Calif.) supplemented with 10% FBS (Hyclone, Logan Utah) or serum-free AIM-V medium (Invitrogen). rhuGM-CSF and IL-4 were gifts from Schering Plough (Kenilworth, N.J.). IL-2 was kindly provided by Chiron Corporation (Emeryville, Calif.). IFNγ, TNFα, and IL-1β were purchased from Strathman Biotech (Germany). Staphylococcus Enterotoxin B (SEB), used for priming high number of naive $CD8^+$ T cells (Mailliard et al., J. Exp. Med. 195:473-483) (2002); Fraser, Res. Immunol., 144:173-174 (1993)), was obtained from Toxin Technologies (Sarasota, Fla.). CD40L-transfected J558 plasmacytoma cells were a gift from Dr. Peter Lane (University of Birmingham, UK) and JY-1 cells were a gift from Dr. Eddy Wierenga (University of Amsterdam). Granzyme B inhibitors IETD-CHO and Z-IETD-fmk were obtained from Calbiochem (San Diego, Calif.).

Isolation of the naive, memory and effector T cell subsets from peripheral blood and tissues. Mononuclear cells, obtained from the peripheral blood of healthy donors, were isolated by density gradient separation using Lymphocyte Separation Medium (Cellgro Mediatech, Hendon Va.). Naive $CD4^+CD45RA^+$ T cells and naive $CD8^+CD45RA^+$ T cells were isolated by negative selection with the StemSep CD4 and CD8 enrichment cocktails, respectively (StemCell Technologies Inc, Vancouver, Canada). Biotinylated anti-CD45RO antibody was used in combination with enrichment cocktails for isolation of naive population. The phenotype of naive $CD8^+CD45RA^+CCR7^+$ T cell population was confirmed by flow cytometry. Tissue-type effector $CD8^+$ T cells were obtained from the liver-metastatic tumor tissue of colorectal cancer patients undergoing surgical resection, and cultured overnight in low dose IL-2 to recover from the isolation-induced stress and possible effects of tumor-derived factors. The memory subset $CD8^+CD45RA-CCR7^+$ T cells from peripheral blood was isolated using CD45RA-depleting/$CD8^+$ T cell enrichment cocktail (StemCell Technologies).

Generation of dendritic cells. Day 6 immature DCs (used as a readout of functional activity of $CD8^+$ T cells), were generated from peripheral blood monocytes cultured ($5 \times 10^5$ per ml) in IMDM/10% FBS supplemented with rhuIL-4 and rhuGM-CSF (both at 1000 U/ml) in 24 well plates (Falcon, Becton Dickinson Labware, N.J.). Type-1 polarized mature DCs, used for the generation of effector- and memory-type $CD8^+$ T cells in vitro, were obtained in serum-free AIM-V medium with IL-4 and GM-CSF, and matured (days 6-8) in the presence of TNFα, IFNγ, IL-1β, IFNα, and poly I:C, as described in Mailliard et al., *Cancer Res.* 64:5934-5937 (2004).

In vitro induction of effector- and memory-type $CD8^+$ T cells. Naive $CD8^+CD45RA^+CCR7$ high T cells ($5 \times 10^5$ cells/well) were activated with SEB pulsed DCs ($5 \times 10^4$ cells/well) in the presence of sCD40L (Alexis Corporation, San Diego, Calif.). Although $CD8^+CD45RA^+$ T cells may contain low frequencies of primed cells, our previous studies showed lack of differences between such cells isolated from adult or cord blood, when using polyclonal models of activation (Mailliard et al., J. Exp. Med. 195:473-483) (2002)). IL-2 (50 U/ml) and IL-7 (5 ng/ml) were added on day 3. Subsequently, culture medium was replenished with fresh medium and cytokines every two days. Priming for 8 days resulted in $CD8^+$ T cells with high content of the cytotoxic granule components Granzyme B and perforin, referred to effector-type $CD8^+$ T cells in the current study. $CD8^+$ T cells primed and cultured for 15 days yielded a functional phenotype of memory cells with low Granzyme B and perforin content. The HLA-A2 restricted $CD8^+$ T cell clone (Mailliard et al., J. Exp. Med. 195:473-483) (2002)) recognizing melanoma antigen gp100 (209-217) was cloned from TIL 1520 cell line provided by Drs Steven Rosenberg and John Wunderlich (National Cancer Institute, Bethesda, Md.), and used either four days after Ag-specific restimulation, or after prolonged culture (>4 weeks) in IL-2 (100 U/ml), in the absence of stimulation.

Modulation of DC function by $CD8^+$ T cells. $CD8^+$ T cells ($5 \times 10^4$ cells) were added to day 6 immature DC cultures with or without antigen SEB (or gp100 peptide). After 48 hours cells were harvested, washed and analyzed by flow cytometry or stimulated with CD40L-transfected J558 cells (Mailliard et al., J. Exp. Med. 195:473-483 (2002)) for 24 hours. For DC protection studies, memory-type $CD8^+$ T cells ($5 \times 10^4$ cells/ml) were added to immature DC cultures 6-8 hours prior to the addition of effector-type $CD8^+$ T cells ($5 \times 10^4$ cells/ml). When indicated, day 8 primed $CD8^+$ T cells were pretreated with the perforin inhibitor (Mailliard et al., J. Exp. Med. 195:473-483 (2002)) Concanamycin A (CMA: 100 nM) for 2 hours and then added to immature DC cultures. The survival of DCs was assessed by staining with nonyl acridine orange dye (NAO; Sigma), as a marker of apoptosis (loss of mitochondrial potential: NAO which binds to mitochondrial cardiolipin in membrane potential dependent manner) (Kanto et al., J. Immunol. 167:3773-3784 (2001)). Light scatter properties and Annexin V staining have been used, yielding similar results (FIG. 7 and data not shown). Briefly, DCs were stained with 0.2 μM NAO in culture medium for 15 minutes at 37° C. The cells were washed and immediately analyzed by flow cytometry. For blocking TNFα function in day 14 memory-type $CD8^+$ T cells, recombinant human soluble TNF-RI (R&D Systems) and anti-human TNFα antibody Infliximab (a gift from Dr. Catharien Hilkens, Newcastle, UK) were added to culture wells with DCs and day 14 memory-type $CD8^+$ T cells.

Flow cytometry. Cell surface phenotype was analyzed by flow cytometry using Beckman Coulter XL. The FITC and PE-labeled isotype controls (mouse IgG1 and IgG2a), anti-human CD86, anti-human perforin were obtained from BD Pharmingen. CD83 monoclonal antibody was purchased from Immunotech and PE-labeled Granzyme B antibody was obtained from Cell Sciences. Goat anti-mouse IgG-FITC conjugated was obtained from Caltag Laboratories. For detection of intracellular PI-9, PI-9 specific mouse monoclonal IgG1 antibody was used as described (Bladergroen et al., *J. Immunol.* 166:3218-3225 (2001)). Briefly, for intracellular staining of PI-9, DCs were washed and then blocked with human Ig for 10 minutes at room temperature. Subsequently, cells were permeabilized with 300 μl of Permiflow (Invirion, Frankfort, Mich.) for 60 minutes at room temperature and then washed. The cells were stained with unconjugated anti human PI-9 antibody for 20 minutes at room temperature followed by staining with FITC conjugated goat anti-mouse IgG antibody. Granzyme B and perforin staining were performed according to manufacturer's protocol, using Permiflow as permeabilization reagent.

Cytokine detection. Concentrations of IL-12, TNFα, IL-5, and IFNγ were determined using specific ELISA, using matched antibody pairs from Endogen. Granzyme B was detected in the supernatants by ELISA (Diaclone, Besancon, France).

Microscopy. For TNFα, Granzyme B, and PI-9 visualization experiments, DCs were cultured on collagen coated cover glass (size 12RD, thinness 1, Propper Manufacturing Co., NY) placed in 24 well plates (Falcon). Before imaging, CD8+ T cells, labeled with either CFSE (2.5 μM) or Calcein blue AM (10 μM) (Molecular Probes) according to manufacturer's protocol, were added to SEB pulsed DCs (day 6) and incubated for 2 hours at 37° C. to allow conjugate formation. Following incubation, cells were fixed with 2% paraformaldehyde, permeabilized with Triton X, and were blocked with normal goat serum (Sigma). The primary antibodies were mouse anti-human Granzyme B (Caltag), rat anti-human TNFα (Serotec), mouse anti-human CD11c-Cy5 (BD Pharmingen), and mouse anti-human PI-9. The secondary antibodies were goat anti-mouse Cy3 Fab 1 fragment and goat anti-rat Cy3 (Jackson ImmunoResearch). All the antibodies were used at final concentration of 5 μg/ml. Fixed and stained DC-CD8 conjugates were imaged with BX51 upright epifluorescence microscope (Olympus) with a 60× objective and image capture was performed using Magnafire software (Optoronix). For PI-9 localization, DC-CD8 conjugates were imaged with Olympus 500 Scanning Confocal Microscope (Olympus) with 60× objective using Fluoview software. All image files were digitally processed using Metamorph or Adobe Photoshop.

A superantigen model (SEB) was used to evaluate the DC-modulating functions of freshly-isolated effector and memory CD8+ T cell subsets and in vitro differentiated naive CD8+ T cells at different stages of activation (Mailliard et al., J. Exp. Med. 195:473-483 (2002); Kalinski et al., J. Immunol., 166:3218-3225 (2001); Kalinski et al., J. Immunol., 165:1877-1881 (2000)). Similar to TCR transgenic mice, this model allows the activation of a high proportion of CD8+ T cells without the need for prior cloning. SEB pulsed immature DCs (day 6) were co-incubated with blood-derived memory CD8+ T cells or tissue-derived effector CD8+ T cells for 48 hours. DC viability was assessed by staining with NAO (Kanto et al., J. Immunol., 167:3773-3784 (2001)). DC activation status was determined by flow cytometric analysis for surface expression of the co-stimulatory molecule CD86 and DC maturation associated marker CD83. IL-12p70 production by DCs following stimulation with J588-CD40L, was measured by ELISA.

In accordance with the observations from the in vivo TCR transgenic mouse models, tissue-isolated effector CD8+ T cells (but not memory or naive CD8+ T cells) rapidly killed immature DCs (FIG. 5A(1)). In sharp contrast, blood-isolated memory CD8+ T cells did not kill DCs, but instead activated the DCs, increasing their expression of the maturation-associated costimulatory molecules (FIGS. 5B(1)-5A(2)). Similar to the IFNγ-dependent ability of naive CD8+ T cells to elevate the IL-12 production in DCs (Mailliard et al., J. Exp. Med. 195:473-483 (2002)), but in contrast to the effector cells, memory CD8+ T cells primed DCs for high production of IL-12p70 upon subsequent stimulation with CD40L (FIG. 5B(2)).

In order to verify that such reciprocal DC-modulating activities of tissue-isolated effector- and blood-isolated memory CD8+ T cells indeed reflect their different stages of differentiation, an SEB-based model of priming of blood-isolated CD8+CD45RA+ T cells (Mailliard et al., J. Exp. Med. 195:473-483 (2002)) was used to study the regulatory functions of the same CD8+ T cell cultures at different time points after activation. Interaction of DCs with the in vitro generated effector- or memory-type CD8+ T cells or with melanoma (gp100)-specific CD8+ T cells, was evaluated at early or late stages of activation. Day 6, immature HLA-A2+DCs were co-cultured with melanoma gp100-specific HLA-A2 restricted CD8+ T cells, in the presence of gp100(209-217) peptide (shaded histograms). Memory-type CD8+ T cells were co-cultured with SEB loaded DCs for 48 hours.

As shown in FIG. 6-IA(1), similar to mouse in vivo models of CD8+ T cell differentiation (34), CD8+ T cells expanded for 6-8 days acquired a Granzyme $B^{high}$, perforin$^{high}$ phenotype, typical of cytotoxic effector cells, and acquired the ability to kill SEB-loaded tumor cells (data not shown). Similar to the tissue-isolated effector cells, such in vitro activated day 6-8 (effector-type) CD8+ T cells effectively killed DCs, as assessed by NAO staining (FIG. 6I-A(1)) or Annexin V (not shown).

Compared to the effector-type CD8+ T cells, the cells activated for more than 14 days (memory-type) expressed reduced levels of Granzyme B and perforin. In contrast to the effector cells, such memory-type CD8+ T cells no longer killed DCs (FIG. 6-IA(2)). Instead, similar to the blood-circulating memory cells, memory-type CD8+ T cells induced DC maturation (manifested by up-regulation of CD86 and CD83) and primed DCs for high production of IL-12p70, the key Th1- and CTL-activating cytokine (Trinchieri et al., Nat. Rev. Immunol. 3:133-146 (2003) (FIG. 6-IIC(1)-(2)).

Activation-dependent differences were also observed in case of CD8+ T cells activated with a HLA-A2-restricted peptide antigen, gp100(209-217). As shown in FIGS. 6B(1)-(2) and 6D(1)-(2), human gp100-specific CD8+ T cell clone rapidly killed immature DCs when being pre-activated with Ag-loaded DCs for four days, but lost such DC-killing function following their prolonged culture in the absence of antigen. Similar to the blood-isolated memory CD8+ T cells and day 14 SEB-activated memory-type cells, such "resting" clonal gp100 CD8+ T cells efficiently induced DC maturation and primed DCs for high IL-12 production (FIG. 6-IID).

The inability of the memory-type CD8+ T cells to kill DCs did not appear to result from any intrinsic defect resulting from long-term cultures, since they regained the ability to kill DCs upon short-term restimulation (data not shown). In these experiments, short-time re-stimulated memory-type CD8+ T cells re-acquire the ability to kill immature DCs. Memory-type CD8+ T cells (day 14-16of culture) were pre-stimulated for 48 hours(or not pre-stimulated) and co-cultured with SEB-pulsed immature DCs (day 6) for 18-20 hours. DC killing and DC activation required the presence of antigen in all the above systems.

These data, in conjunction with the results obtained using blood-isolated memory cells (FIG. 5A(1)-(2)), indicate that after a transient period of DC-killing activity, activated CD8+ T cells enter a "helper phase" of their activation cycle. Similar termination of the suppressor phase of activity has also been observed in case of tissue-isolated effector cells (data not shown).

EXAMPLE 5

This example demonstrates the role of perforin/Granzyme B- and Fas/Fas-L-mediated cytotoxic pathways in the killing of human DCs by effector CD8+ T cells.

Cells were cultured as described in Example 4. Release of functional perforin was blocked by either pre-treatment of the effector-type CD8+ T cells with CMA (100 nM) or by the addition of EGTA (4 mM) during DC-CD8 co-culture. The survival of DCs was analyzed by change in the light scatter properties, as indicated by dot plots in FIG. 7A(1), and verified using the NAO staining, shown in FIG. 7A(2). As shown in FIG. 7A(1), DC killing was completely eliminated by the addition of EGTA or Concanamycin A (CMA), the inhibitors of the perforin-dependent (but not Fas/Fas-L-dependent) pathway of CTL-mediated killing (Kataoka et al., *J. Immunol.*, 156:3678-3686 (1996); Grossman et al., *Immunity* 21:589-601 (2004)). In contrast, no inhibition of DC killing was observed in the presence of the Fas-L antagonist (data not shown).

CMA-treated effector-type CD8+ T cells were co-cultured with SEB loaded DCs for 48 hours. CMA-treated (perforin-blocked) effector-type CD8+ T cells were prepared, and TNFα (50 ng/ml) induced DC maturation was used as positive control. The treated CD8+ T cells were found to enhance DC activation (FIG. 7B). CMA-treated (perforin-blocked) effector-type CD8+ T cells were also found to induce type-1 polarized phenotype in DCs, characterized by enhanced ability to produce IL-12p70. As shown in FIGS. 7B, C, pre-treatment of the effector cells with CMA abrogated their DC-killing ability, resulting in the induction of phenotypic maturation of the DCs (TNFγ was used as a control for DC maturation) and their priming for high IL-12p70 production.

Dendritic cells pretreated (1 hour) with IETD-CHO (200 µM) or Z-IETD-fmk (20 µM), were co-cultured with effector-type CD8+ T cells. Survival of DCs was analyzed after 10-12 hours. Similar to the blocking of the perforin pathway, pre-treatment of DCs with the specific Granzyme B inhibitors IETD-CHO or Z-IETD-fmk (Thornberry et al., *J. Biol. Chem.* 272: 17907-17911 (1997)), abrogated the CTL-induced DC death (FIG. 7D).

These results indicate that the perforin- and Granzyme B-mediated cytolytic pathway is the principal mode of DC elimination by human effector CD8+ T cells, and that, in its absence, the effector cells no longer suppress DC activity, but support it.

EXAMPLE 6

This example demonstrates that the initial interaction of DCs with memory-type CD8+ T cells may protect DC from the eventually-acquired CTL activity of the same cells.

Memory-type CD8+ T cells were unable to kill DCs even after 48 hour co-cultures although their killing function can be restored following re-activation (FIG. 7E), and in mouse models, 30-96 hour-reactivated effector-memory and central-memory cells re-acquire their DC-killing potential (Hermans et al., *J. Immunol.*, 164:3095-3101 (2000); Belz et al., PNAS 104:6341-6346 (2007); Guarda et al., *Nat. Immunol.* 8:743-750 (2007)). In order to test this possibility, DCs were exposed first to memory-type CD8+ T cells, followed by co-culture with effector-type CD8+ T cells.

Memory CD8+ T cells or CD4+ Th cells were co-cultured with SEB-loaded DCs for 8-10 hours, followed by the addition of effector CD8+ T cells. DC viability was assessed by NAO staining at 24 hours. As shown in FIG. 8A, the DCs exposed to memory-type CD8+ T cells became resistant to subsequent killing by CTLs. This protective effect of the memory-type CD8+ T cells was similar to that exerted by activated CD4+ T cells, the classical helper T cells (FIG. 8A), which have been proposed to mediate their helper function by DC protection (Mueller et al., *J. Immunol.* 176:7379-7384 (2006); Medema et al., *J. Exp. Med.* 194:657-667 (2001)).

DCs exposed to memory-type CD8+ T cells, CD4+ T cells (or CD40L) were stained for intracellular PI-9. Rapid induction of PI-9 in DCs exposed to memory-type CD8+ T cells was visualized by confocal microscopy.

In further support of the similarity between the helper functions of CD4+ T cells And CD8+ memory T cells, DCs that interacted with either of these T cell subsets expressed similar levels of an endogenous Granzyme B inhibitor PI-9 (FIG. 8B), a human equivalent of murine serine protease inhibitor (SPI-6) (Sun et al., *J. Biol. Chem* 272:15434-15441 (1997)) shown to mediate the protection of mouse DCs from CTL-mediated killing (Medema et al., *J. Exp. Med.* 194:657-667 (2001)). The analysis of PI-9 expression at the per cell basis, using confocal microscopy, revealed that PI-9 is massively up-regulated in DCs within 2 hours following their interaction with memory-type CD8+ T cells, with PI-9 expression being detectable in the individual DCs interacting with T cells already within 15 minutes (Data shown in FIG. 4C of Watchmaker et al., *J. Immunol.* 2008 Mar. 15:). 180(6): 3857-65. Similar kinetics of PI-9 induction was observed in DCs exposed to recombinant TNFα (FIG. 8C).

Intracellular expression of PI-9 (open profiles) in DCs has been analyzed by flow cytometry before and after (15 and 120 minutes) the exposure to recombinant TNFα (50 ng/ml).

Immature DCs were pre-treated with rhuTNFα (100 ng/ml; 24 hours) prior to co-cultures with effector CD8+ T cells. Different relative kinetics of the TNFα versus Granzyme B release in memory and effector CD8+ T cells during the interaction with DCs are shown in FIGS. 9C and D.

Additionally, the CTL-protecting helper activity of memory-type CD8+ T cells is mediated by TNFα and can be blocked by the addition of soluble TNF receptor I (blocking potential actions of TNFα and LT) or TNFα-specific antibody (Infliximab; blocking TNFα exclusively). In accordance with the role of TNFα (rather than LT), both reagents proved equally effective in converting the memory T cell-induced DC activation into memory T cell-induced DC death (FIG. 9A, data not shown for sTNF-RI). Blood-isolated naive CD8+ or CD4+ T cells were primed with the SEB-loaded immature DCs in the absence or presence of a-irradiated memory-type or effector-type CD8+ T cells. The expanding cultures of naive CD8+ or CD4+ T cells were harvested, respectively at day 5 or day 10, counted and tested for their functional activity, using CTL assay or the analysis of their Th1/Th2 cytokine profiles. CTL activity of CD8+ T cell cultures performed in the presence or absence of memory or effector CD8+ T cells was assessed by 51Cr release assay, using SEB-loaded JY-1 cells as targets. Naive CD4+ T cells primed in the presence of memory-type CD8+ T cells develop a strongly polarized Th1 cytokine profile as determined by ELISA.

As expected, these effects were accompanied by the prevention of the induction of PI-9 in DCs (FIG. 9B). On the other hand, DCs exposed to exogenous TNFα acquired resistance to CTL killing (FIG. 9C).

In accordance with the different outcome of interaction of memory versus effector T cells with DCs, a significant release of TNFα occurred within two hours of interaction of DCs with memory-type CD8+ T cells, whereas the release of Granzyme B by memory-type CD8+ T cells was significant only at later time points. Effector T cells, however, Simultaneously released both TNFα and Granzyme B (FIG. 9D). Furthermore, the microscopic analysis of the DC-T cell interactions (at the 2 hour time point, when PI-9 is induced in DCs: see FIG. 8C-D) demonstrated equivalent mobilization of TNFα in both memory-type and effector-type CD8+ T cells, whereas exclusively the effector CD8+ T cells, but not memory cells, directed Granzyme B-containing cytotoxic granules towards the contact zone with DCs (Data shown at FIG. 5F-G of Watchmaker et al., *J. Immunol*. 2008 Mar. 15;180(6):3857-65. This sequence of events indicates that the early TNFα release by the memory CD8+ T cells induces early PI-9 expression and protects DC from the subsequently-released Granzyme B.

In support of their ability to perform respective suppressor and helper functions during the de novo induction of type-1 immune cells, CD8+ T cells at different stages of activation differentially regulated the expansion of naive CD8+ and CD4+ T cells and the development of their respective CTL and Th1 functions (FIGS. 10A, B). In accordance with the role of memory CD8+ T cells in regulating the survival and function of DCs (see FIG. 8), the helper signals from memory CD8+ T cells not only promoted the DC-driven functional differentiation of naive T cells but were also able to fully counteract the suppressive activity of effector CD8+ T cells, resulting in the effective induction of functional CTL and Th1 responses even in the presence of effector CD8+ T cells (FIG. 10).

EXAMPLE 7

This example demonstrates the use of Granzyme-B inhibitors in modifying the activity of DCs to induce high numbers of tumor-specific CTLs ex vivo, as a therapeutic agent for adoptive T cell transfer therapies.

Methods: Dendritic cells loaded with tumor-relevant antigens are used to sensitize (Mailliard et al., *Cancer Res*. 64:5934-5937 (2004)) the patients' autologous CD8+ T Cells (or possibly bulk T cell population, containing both CD4+ and CD8+ T cells, in the absence of presence of the inhibitors of CTL function (such as CMA) or the inhibitors of CTL-induced DC killing (for example synthetic cell-permeable versions of peptide inhibitors of Caspases or Granzymes such as IETD or DEVD, or similar).

Following the expansion of the emerging tumor-specific CD8+ T cells (or CD8+ and CD4+ T cells) (and possible additional rounds of in vitro sensitization), the cell yields of the de novo-induced Th cells and CTLs and their ability to perform effector functions (Th1-type cytokine profile and CTL activity) are determined. The cells obtained in the presence of CTL function, expected to contain higher numbers of tumor-specific cells and to be more effective at the per cell basis in their ability to kill tumor cells.

As an alternative to the application of separate antigenic peptides and GrB-inhibiting peptides, the above-described in vitro sensitizing (IVS) cultures can be involve a longer peptide construct, composed of a peptide fragment conferring the inhibitory activity (such as IETD, DEVD, or similar) possible additional sequences conferring cell-permeability to the peptide (for example the hydrophobic region of the signal peptide of K-FGF, peptide, and a tumor-relevant antigenic peptide. Such poly-peptide constructs can be either synthesized as "direct conjugates (back-to-back linkage of different components) or as "indirect" conjugates containing an additional peptide sequence (a "linker"), facilitating intracellular cleavage of the multivalent construct.

Peptide constructs including tumor antigens (for example, MART-$1_{27-35}$ or CEA$_{CAP-1}$), between the permeability domain and inhibitory domains, or placed on each side of the inhibitory construct are prepared.

The ability of native MART-$1_{27-35}$ or CEA$_{CAP-1}$ peptides and the respective inhibitory peptide constructs to induce CTL responses are evaluated in an in vitro sensitization system, previously used to demonstrate the advantage of the cytokine-based DC1 polarization for the induction of melanoma-specific CTLs (see above).

The results of these experiments indicate that the DCs interacting with T$_{eff}$ in the presence of GrB- or Pfn inhibitors do not die but acquire a mature phenotype, associated with elevated production of the key Th1- and CTL-driving cytokine, IL-12p70 (type-1 DC polarization). In the absence of DC killing, T$_{eff}$ cells may perform an analogous "helper" function to T$_{mem}$ cells, supporting the ability of DCs to activate additional CD4+ and CD8+ T cells and activate their Th1 and CTL functions, desirable in fighting cancer.

EXAMPLE 8

This example demonstrates the therapeutic activity of peptide-based vaccines utilizing GrB inhibitors in vivo.

GrB\Caspase-3 and Caspase-8 inhibitors are used as components of modified peptide vaccines comprising a tumor-specific peptide epitope and a selected apoptosis inhibitor. Such membrane-permeable peptide inhibitors can contain an inhibitory peptide domain linked to a membrane-permeability-conferring domain. The additional attachment of an antigenic component does not eliminate their inhibitory activity. Generation of peptide constructs acting as a source of antigens and conferring the resistance of endogenous DCs (that take up such vaccines in vivo) to tumor-specific CTLs (and allowing them to receive polarizing signals, see FIG. 7) are used to prepare single "off-the-shelf" vaccines against cancers with well-defined rejection antigens, such as melanoma.

"Direct" or "Indirect" linker-containing conjugates of SIINFEKL with IEDT (DEVD, or other peptide inhibitors of apoptotic pathway) are synthesized. Tumor-relevant antigenic component are included between the permeability domain and inhibitory domains, or alternatively at either end of the inhibitor.

In order to test the activity of the modified antigenic peptides can act as anticancer vaccines, mice are inoculated with the antigenically-relevant tumor cells and receive (multiple doses) with: (1) no treatment; (2) Tumor Ag alone; (3) IEDT (or DEVD); (4) Tumor Ag-IEDT conjugate (or similar construct containing alternative inhibitor;); (5) Tumor Ag (unconjugated) plus IEDT (or alternative inhibitor;) injected locally; (6) Tumor Ag (unconjugated) plus IEDT (or alternative inhibitor;) injected on the opposite flank.

The ability of IEDT to protect DCs from tumor-specific CTL-mediated killing and to promote their polarization by CTL are expected to allows the endogenous DCs exposed in vivo to this peptide-based vaccine to mediate superior immunogenic and antitumor function (tumor shrinkage or slower tumor growth). These effects are expected to be particularly pronounced in case of the physical incorporation of tumor-relevant Ag into the inhibitor constructs (group 4), but may also be present if the antigenic and anti-apoptotic peptides are co-administered separately (group 5 and possibly 6) is also observed.

These results demonstrate the use of inhibitory agents in combination with cancer-associated antigens in vivo to modulate polarization of DCs in vivo.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of vaccinating a patient against a target antigen comprising:
   (a) administering a sensitizing composition comprising a non-target antigen to a patient; and
   (b) administering a therapeutic composition comprising a non-target antigen and the target antigen to the patient,
   wherein the non-target antigen in the sensitizing composition is the same as or different than the non-target antigen in the therapeutic composition, and wherein the therapeutic composition is administered after the sensitizing composition, at an interval sufficient for induction of memory T cells, whereby the patient is vaccinated against the target antigen.

2. The method of claim 1, wherein the non-target antigen of the sensitizing composition is the same as the non-target antigen of the therapeutic composition.

3. The method of claim 1 wherein the sensitizing composition comprises multiple non-target antigens.

4. The method of claim 3, wherein the therapeutic composition comprises at least one non-target antigen of the sensitizing composition.

5. The method of claim 3, further comprising administering one or more additional therapeutic compositions each comprising the target antigen and a non-target antigen.

6. The method of claim 5, wherein each non-target antigen is distinct.

7. The method of claim 6, wherein the therapeutic compositions are administered cyclically.

8. The method of claim 1, wherein the non-target antigen comprises an epitope from a source selected from the group consisting of viral, bacterial, protozoan, helminthic, mycobacterial, alloantigenic, and xenoantigenic.

9. The method of claim 8, wherein the epitope is from a viral source, and wherein the virus is selected from the group consisting of hepatitis, Herpes simplex, cytomegalovirus (CMV), Epstein-Barr Virus (EBV) and other herpes viruses, Hepatitis B Virus (HBV), Hepatitis C Virus (HCV), and influenza virus.

10. The method of claim 1, wherein the target antigen is a tumor antigen or an antigen from an infectious agent.

11. The method of claim 10, wherein the target antigen is a tumor antigen, and wherein the tumor is an adenocarcinoma.

12. A method of vaccinating a patient against a target antigen, the patient having memory-type immunity to a non-target antigen, the method comprising:
   a. determining the presence of memory-type immunity to a non-target antigen in a patient; and
   b. administering a therapeutic composition comprising the non-target antigen and the target antigen to the patient, wherein the patient was found to have memory-type immunity to the non-target antigen in (a);
   whereby the patient is vaccinated against the target antigen, and wherein the target antigen is a tumor antigen or an antigen from a virus, bacteria, protozoa, or parasite.

13. The method of claim 12, further comprising administering to the patient one or more additional therapeutic compositions comprising the target antigen and a non-target antigen, wherein the patient was determined to have immunity to the non-target antigen in (a).

14. The method of claim 13, wherein (a) comprises determining the presence of memory-type immunity to multiple non-target antigens, wherein each of said non-target antigens is distinct.

15. The method of claim 14, wherein the therapeutic compositions are administered cyclically.

16. The method of claim 12, wherein the non-target antigen comprises an epitope from a source selected from the group consisting of viral, bacterial, protozoan, helminthic, mycobacterial, alloantigenic, and xenoantigenic.

17. A method of vaccinating a patient against a target antigen, the patient having immunity to a non-target antigen, the method comprising:
   (a) determining immunity to a non-target antigen in a patient;
   (b) isolating a sample of dendritic cells from the patient;
   (c) loading the dendritic cells with the target antigen and a the non-target antigen, wherein the patient was found to have immunity to the non-target antigen in (a), and wherein the target antigen is a tumor antigen or an antigen from an infectious agent; and;
   (d) administering to the patient a therapeutic composition comprising the loaded dendritic cells;
   whereby the patient is vaccinated against the target antigen.

18. The method of claim 17, further comprising administering to the patient one or more additional therapeutic compositions comprising dendritic cells loaded with the target antigen and a non-target antigen to which the patient has immunity, wherein the patient was determined to have immunity to the non-target antigen in (a).

19. The method of claim 18, wherein (a) comprises determining the presence of immunity to multiple non-target antigens, wherein each of said non-target antigens is distinct.

20. The method of claim 18, wherein the therapeutic compositions are administered cyclically.

21. The method of claim 17, wherein the non-target antigen comprises an epitope from a source selected from the group consisting of viral, bacterial, protozoan, helminthic, mycobacterial, alloantigenic, and xenoantigenic.

* * * * *